US009848773B2

United States Patent
Su

(10) Patent No.: US 9,848,773 B2
(45) Date of Patent: Dec. 26, 2017

(54) DISPOSABLE CAP FOR AN EYE IMGING APPARATUS AND RELATED METHODS

(71) Applicant: Visunex Medical Systems Co. Ltd., Grand Cayman (KY)

(72) Inventor: Wei Su, Sunnyvale, CA (US)

(73) Assignee: VISUNEX MEDICAL SYSTEMS CO. LTD., Grand Cayman (KY)

( * ) Notice: Subject to any disclaimer, the term of this patent is extended or adjusted under 35 U.S.C. 154(b) by 0 days.

(21) Appl. No.: 15/007,101

(22) Filed: Jan. 26, 2016

(65) Prior Publication Data

US 2016/0213250 A1 Jul. 28, 2016

Related U.S. Application Data

(60) Provisional application No. 62/107,993, filed on Jan. 26, 2015.

(51) Int. Cl.
*A61B 3/00* (2006.01)
*A61B 3/125* (2006.01)
(Continued)

(52) U.S. Cl.
CPC ............... *A61B 3/125* (2013.01); *A61B 3/15* (2013.01); *A61B 46/10* (2016.02); *A61B 50/30* (2016.02);
(Continued)

(58) Field of Classification Search
CPC ...................................................... A61B 3/125
(Continued)

(56) References Cited

U.S. PATENT DOCUMENTS

| 3,301,627 A | 1/1967 | Kimura |
| 3,373,864 A * | 3/1968 | Neely ............... A61J 11/00 206/471 |

(Continued)

FOREIGN PATENT DOCUMENTS

| CN | 1170343 A | 1/1998 |
| CN | 101953675 A | 1/2011 |

(Continued)

OTHER PUBLICATIONS

STIC Search Report, Eileen Patton, Mar. 29, 2016.*

(Continued)

*Primary Examiner* — Stephone B Allen
*Assistant Examiner* — Travis Fissel
(74) *Attorney, Agent, or Firm* — Artegis Law Group, LLP

(57) ABSTRACT

Disclosed herein is a disposable cap for an eye imaging apparatus with an optical window and related methods. The disposable cap can comprise an optically transparent window cover, a ridge, a side wall and a locking element. The window cover can comprise a convex back surface to match a concave shape of the optical window. The ridge of the disposable cap can extend distally and radially outward from the window cover and the side wall can extend proximally and radially outwardly from the ridge. The locking element can comprise one or more radially inward projections and one or more radially outward releasing tabs. A disposable packaging shell of the disposable cap also disclosed. Disclosed herein is also a plug-in disposable system comprising the disposable cap and the disposable packaging shell, configured to enable the disposable cap to be attached to and detached from the eye imaging apparatus.

23 Claims, 22 Drawing Sheets

(51) Int. Cl.
*A61B 3/15* (2006.01)
*A61B 50/30* (2016.01)
*A61B 46/10* (2016.01)
*A61B 50/00* (2016.01)
*A61B 17/00* (2006.01)

(52) U.S. Cl.
CPC .............. *A61B 2017/00902* (2013.01); *A61B 2050/005* (2016.02); *A61B 2050/0051* (2016.02); *A61B 2050/0054* (2016.02); *A61B 2050/0066* (2016.02); *A61B 2050/0084* (2016.02); *A61B 2050/3015* (2016.02)

(58) Field of Classification Search
USPC ........................................................ 351/219
See application file for complete search history.

(56) References Cited

U.S. PATENT DOCUMENTS

| | | | |
|---|---|---|---|
| 3,944,341 A | 3/1976 | Pomerantzeff | |
| 4,023,189 A | 5/1977 | Govignon | |
| 4,026,638 A | 5/1977 | Govignon | |
| 4,230,403 A | 10/1980 | Hashimoto et al. | |
| 4,247,190 A | 1/1981 | Hashimoto et al. | |
| 4,357,088 A | 11/1982 | Pomerantzeff | |
| 4,461,551 A | 7/1984 | Blaha | |
| 4,659,203 A | 4/1987 | Niwa et al. | |
| 5,036,446 A | 7/1991 | Quintanilla et al. | |
| 5,046,608 A | 9/1991 | Laipply | |
| 5,156,456 A | 10/1992 | Hoftman et al. | |
| 5,309,186 A | 5/1994 | Mizuno | |
| 5,343,861 A | 9/1994 | Herman | |
| 5,455,644 A | 10/1995 | Yazawa et al. | |
| 5,506,634 A | 4/1996 | Wei et al. | |
| 5,537,127 A | 7/1996 | Jingu | |
| 5,537,162 A | 7/1996 | Hellmuth et al. | |
| 5,543,865 A | 8/1996 | Nanjo | |
| 5,608,472 A | 3/1997 | Szirth et al. | |
| 5,745,212 A | 4/1998 | Volk | |
| 5,751,396 A | 5/1998 | Masuda et al. | |
| 5,822,036 A | 10/1998 | Massie et al. | |
| 6,065,837 A | 5/2000 | Goldfain et al. | |
| 6,089,761 A | 7/2000 | Sakurai | |
| 6,092,898 A | 7/2000 | De Juan, Jr. | |
| 6,267,752 B1 | 7/2001 | Svetliza | |
| 6,269,222 B1 | 7/2001 | Hartung | |
| 6,296,358 B1 | 10/2001 | Cornsweet et al. | |
| 6,305,804 B1* | 10/2001 | Rice .................. A61B 3/1233 351/221 | |
| 6,361,167 B1 | 3/2002 | Su et al. | |
| 6,409,341 B1 | 6/2002 | Goldfain et al. | |
| 6,446,795 B1 | 9/2002 | Allen et al. | |
| 6,535,650 B1 | 3/2003 | Poulo et al. | |
| 6,636,696 B2 | 10/2003 | Saito | |
| 6,685,317 B2 | 2/2004 | Su et al. | |
| 6,761,455 B2 | 7/2004 | Sumiya | |
| 6,801,913 B2* | 10/2004 | Matsumura ........... G06F 19/327 | |
| 7,025,459 B2 | 4/2006 | Cornsweet et al. | |
| 7,048,379 B2 | 5/2006 | Miller et al. | |
| 7,147,329 B2 | 12/2006 | Stone et al. | |
| 7,156,518 B2 | 1/2007 | Cornsweet et al. | |
| 7,261,416 B2 | 8/2007 | Nishio et al. | |
| 7,306,336 B2 | 12/2007 | Akita et al. | |
| 7,347,553 B2 | 3/2008 | Matsumoto | |
| 7,357,248 B2 | 4/2008 | Sivakumar et al. | |
| 7,360,895 B2 | 4/2008 | Cornsweet et al. | |
| 7,387,385 B2 | 6/2008 | Sander | |
| 7,401,628 B2 | 7/2008 | Gleichauf et al. | |
| 7,445,335 B2 | 11/2008 | Su et al. | |
| 7,448,753 B1 | 11/2008 | Chinnock | |
| 7,499,634 B2 | 3/2009 | Yogesan et al. | |
| 7,508,524 B2 | 3/2009 | Mahadevan-Jansen et al. | |
| 7,568,802 B2 | 8/2009 | Phinney et al. | |
| 7,621,636 B2 | 11/2009 | Su et al. | |
| 7,621,638 B2 | 11/2009 | Su et al. | |
| 7,650,064 B2 | 1/2010 | Isogai et al. | |
| 7,667,187 B2 | 2/2010 | Grigo et al. | |
| 7,677,730 B2 | 3/2010 | Shimizu | |
| 7,731,361 B2 | 6/2010 | Honda | |
| 7,802,884 B2 | 9/2010 | Feldon et al. | |
| 7,815,310 B2 | 10/2010 | Su et al. | |
| 7,824,035 B2 | 11/2010 | Yamada et al. | |
| 7,854,510 B2 | 12/2010 | Verdooner et al. | |
| 7,986,859 B2 | 7/2011 | Fischer | |
| 8,002,410 B2 | 8/2011 | Shea | |
| 8,011,504 B1* | 9/2011 | Farberov ........... A61B 1/00135 206/316.1 | |
| 8,049,899 B2 | 11/2011 | Waelti et al. | |
| 8,064,989 B2 | 11/2011 | Brown et al. | |
| 8,103,061 B2 | 1/2012 | Payonk et al. | |
| 8,111,874 B2 | 2/2012 | Chan | |
| 8,115,830 B2 | 2/2012 | Kato et al. | |
| 8,118,431 B2 | 2/2012 | Shea et al. | |
| 8,218,066 B2 | 7/2012 | Tsukatani et al. | |
| 8,237,805 B2 | 8/2012 | Nozaki | |
| 8,313,195 B2 | 11/2012 | Itoh et al. | |
| 8,328,356 B2 | 12/2012 | Cheng et al. | |
| 8,330,808 B2 | 12/2012 | Satake | |
| 8,356,900 B2 | 1/2013 | Zhou et al. | |
| 8,368,771 B2 | 2/2013 | Kino | |
| 8,421,855 B2 | 4/2013 | Buckland et al. | |
| 8,449,112 B2 | 5/2013 | Kishida | |
| 8,449,115 B2 | 5/2013 | Aikawa et al. | |
| 8,459,794 B2 | 6/2013 | Juhasz et al. | |
| 8,480,232 B2 | 7/2013 | Aikawa | |
| 8,506,082 B2 | 8/2013 | Saito | |
| 8,506,083 B2 | 8/2013 | Zhou et al. | |
| 8,518,109 B2 | 8/2013 | Shea et al. | |
| 8,540,104 B2 | 9/2013 | Elenes | |
| 8,550,650 B1 | 10/2013 | McGinty | |
| 8,561,135 B2 | 10/2013 | Upp | |
| 8,562,135 B2 | 10/2013 | Endo | |
| 8,594,757 B2 | 11/2013 | Boppart et al. | |
| 8,627,549 B2 | 1/2014 | Vernieu | |
| 8,768,161 B2 | 7/2014 | Ono et al. | |
| 8,777,413 B2 | 7/2014 | Zhou et al. | |
| 8,811,745 B2 | 8/2014 | Farsiu et al. | |
| 8,820,929 B2 | 9/2014 | Shea et al. | |
| 8,820,931 B2 | 9/2014 | Walsh et al. | |
| 8,860,796 B2 | 10/2014 | Buckland et al. | |
| 8,861,061 B1* | 10/2014 | Graham ................. A61B 3/117 359/219.1 | |
| 8,896,842 B2 | 11/2014 | Bower et al. | |
| 8,926,350 B2 | 1/2015 | Wolfe et al. | |
| 8,955,971 B2 | 2/2015 | Ichikawa et al. | |
| 8,967,807 B2 | 3/2015 | Mizuno | |
| 8,985,119 B1 | 3/2015 | Webb et al. | |
| 9,022,568 B2 | 5/2015 | Shikaumi | |
| 9,022,569 B2 | 5/2015 | Nakahara et al. | |
| 9,106,831 B2 | 8/2015 | Miyamoto et al. | |
| 9,119,563 B2 | 9/2015 | Buckland et al. | |
| 9,149,179 B2 | 10/2015 | Barnard et al. | |
| 9,155,466 B2 | 10/2015 | Su | |
| 9,171,351 B2 | 10/2015 | Kita | |
| 9,179,840 B2 | 11/2015 | Su | |
| 9,211,064 B2 | 12/2015 | Wang | |
| 9,265,426 B2 | 2/2016 | Zuluage | |
| 2001/0028438 A1 | 10/2001 | Matsumoto | |
| 2002/0097379 A1 | 7/2002 | Goldfain et al. | |
| 2002/0180727 A1 | 12/2002 | Guckenberger et al. | |
| 2003/0174211 A1 | 9/2003 | Imaoka et al. | |
| 2004/0118431 A1 | 6/2004 | Flynn | |
| 2005/0018135 A1 | 1/2005 | Maeda et al. | |
| 2005/0039565 A1 | 2/2005 | Minkow et al. | |
| 2005/0270484 A1 | 12/2005 | Maeda et al. | |
| 2005/0284774 A1* | 12/2005 | Mordaunt ............. A61B 3/125 206/5.1 | |
| 2006/0069312 A1 | 3/2006 | O'Connor | |
| 2006/0114411 A1 | 6/2006 | Wei et al. | |
| 2006/0176447 A1 | 8/2006 | Reis | |
| 2006/0257138 A1 | 11/2006 | Fromm | |
| 2007/0188699 A1 | 8/2007 | Cech et al. | |
| 2007/0236663 A1 | 10/2007 | Waldorf et al. | |

(56) References Cited

U.S. PATENT DOCUMENTS

| | | |
|---|---|---|
| 2007/0244393 A1 | 10/2007 | Oshiki et al. |
| 2008/0033371 A1* | 2/2008 | Updegraff ............ A61M 39/162 604/263 |
| 2008/0071254 A1 | 3/2008 | Lummis et al. |
| 2008/0211420 A1 | 9/2008 | Walker et al. |
| 2009/0141237 A1 | 6/2009 | Izatt et al. |
| 2009/0153797 A1 | 6/2009 | Allon et al. |
| 2009/0185135 A1* | 7/2009 | Volk ...................... A61B 3/125 351/219 |
| 2009/0211586 A1* | 8/2009 | Shea ...................... A61B 3/00 128/849 |
| 2010/0091244 A1 | 4/2010 | Volk |
| 2010/0118270 A1* | 5/2010 | Shea ...................... A61B 3/117 351/219 |
| 2010/0149490 A1 | 6/2010 | Olivier et al. |
| 2010/0184479 A1 | 7/2010 | Griffin |
| 2010/0201604 A1 | 8/2010 | Kee et al. |
| 2010/0217080 A1 | 8/2010 | Cheung et al. |
| 2010/0228236 A1 | 9/2010 | Muhlhoff et al. |
| 2010/0253907 A1 | 10/2010 | Korb et al. |
| 2010/0278394 A1 | 11/2010 | Raguin et al. |
| 2011/0051086 A1 | 3/2011 | Takai et al. |
| 2011/0052205 A1 | 3/2011 | Yu et al. |
| 2011/0085137 A1 | 4/2011 | Kleen et al. |
| 2011/0090460 A1 | 4/2011 | Graham et al. |
| 2011/0103655 A1 | 5/2011 | Young et al. |
| 2011/0176109 A1 | 7/2011 | Mann |
| 2011/0234977 A1 | 9/2011 | Verdooner |
| 2011/0267583 A1 | 11/2011 | Hayashi |
| 2011/0299036 A1 | 12/2011 | Goldenholz |
| 2012/0013140 A1 | 1/2012 | Nitkin |
| 2012/0026461 A1 | 2/2012 | Chou et al. |
| 2012/0050683 A1 | 3/2012 | Yates |
| 2012/0092619 A1 | 4/2012 | Rowe |
| 2012/0099077 A1 | 4/2012 | Abt |
| 2012/0138503 A1* | 6/2012 | Patel .................... B65D 1/0215 206/524.7 |
| 2012/0162602 A1 | 6/2012 | Huening et al. |
| 2012/0222977 A1* | 9/2012 | Elenes ................ B65D 25/287 206/316.1 |
| 2012/0224142 A1 | 9/2012 | Cornsweet et al. |
| 2012/0229617 A1 | 9/2012 | Yates et al. |
| 2012/0249748 A1 | 10/2012 | Nagano |
| 2012/0274900 A1 | 11/2012 | Horn et al. |
| 2012/0287255 A1 | 11/2012 | Ignatovich et al. |
| 2012/0300998 A1 | 11/2012 | Loudovski et al. |
| 2012/0320583 A1 | 12/2012 | Van Bommel et al. |
| 2013/0033593 A1 | 2/2013 | Chinnock et al. |
| 2013/0044200 A1 | 2/2013 | Brill et al. |
| 2013/0057828 A1 | 3/2013 | De Smet |
| 2013/0064536 A1 | 3/2013 | Taki et al. |
| 2013/0096390 A1 | 4/2013 | Weller-Brophy et al. |
| 2013/0103014 A1 | 4/2013 | Gooding et al. |
| 2013/0135584 A1 | 5/2013 | Alasaarela et al. |
| 2013/0160621 A1 | 6/2013 | Marsden et al. |
| 2013/0182895 A1 | 7/2013 | Touzov et al. |
| 2013/0235345 A1 | 9/2013 | Ohban |
| 2013/0261610 A1 | 10/2013 | LaConte et al. |
| 2013/0271728 A1 | 10/2013 | Ranchod |
| 2013/0301003 A1 | 11/2013 | Wells et al. |
| 2013/0321906 A1 | 12/2013 | Kriofske et al. |
| 2014/0055749 A1 | 2/2014 | Zhou et al. |
| 2014/0063455 A1 | 3/2014 | Zhou et al. |
| 2014/0063456 A1 | 3/2014 | Zhou et al. |
| 2014/0063457 A1 | 3/2014 | Zhou et al. |
| 2014/0063459 A1 | 3/2014 | Zhou et al. |
| 2014/0063462 A1 | 3/2014 | Zhou et al. |
| 2014/0063463 A1 | 3/2014 | Zhou et al. |
| 2014/0085603 A1 | 3/2014 | Su et al. |
| 2014/0111768 A1 | 4/2014 | Komine |
| 2014/0125949 A1 | 5/2014 | Shea et al. |
| 2014/0152955 A1 | 6/2014 | Papageorgiou et al. |
| 2014/0221826 A1 | 8/2014 | Joos et al. |
| 2014/0226128 A1 | 8/2014 | Lawson et al. |
| 2014/0232987 A1 | 8/2014 | Westphal et al. |
| 2014/0268037 A1 | 9/2014 | Siminou |
| 2014/0293033 A1 | 10/2014 | Takii |
| 2014/0307226 A1 | 10/2014 | Lathrop et al. |
| 2014/0347628 A1 | 11/2014 | Martinez Corral et al. |
| 2014/0375952 A1 | 12/2014 | Hanebuchi |
| 2015/0009473 A1 | 1/2015 | Su |
| 2015/0021228 A1 | 1/2015 | Su et al. |
| 2015/0335242 A1 | 11/2015 | Saito |
| 2015/0366447 A1 | 12/2015 | Su et al. |
| 2015/0374235 A1 | 12/2015 | Reimer et al. |
| 2016/0007850 A1 | 1/2016 | Su |
| 2016/0007956 A1 | 1/2016 | Mauldin et al. |
| 2016/0008169 A1 | 1/2016 | Yu |
| 2016/0029887 A1 | 2/2016 | Su |
| 2016/0073877 A1 | 3/2016 | Su et al. |
| 2016/0073878 A1 | 3/2016 | Su et al. |

FOREIGN PATENT DOCUMENTS

| | | |
|---|---|---|
| EP | 1289407 B1 | 12/2009 |
| EP | 2164383 A2 | 3/2010 |
| EP | 1928297 B1 | 11/2010 |
| EP | 2296531 A1 | 3/2011 |
| EP | 2312994 A2 | 4/2011 |
| EP | 2334222 A2 | 6/2011 |
| EP | 2066226 B1 | 12/2012 |
| EP | 2790570 A1 | 10/2014 |
| EP | 2845534 A1 | 3/2015 |
| JP | 2002238853 A | 8/2002 |
| TW | 201204314 A1 | 2/2012 |
| WO | WO03/057024 A1 | 7/2003 |
| WO | WO2006/013579 A1 | 2/2006 |
| WO | WO2010009450 A1 | 1/2010 |
| WO | WO2010/096756 A1 | 8/2010 |
| WO | WO2010/108228 A1 | 9/2010 |
| WO | WO2010117386 A1 | 10/2010 |
| WO | WO2011/022803 A1 | 3/2011 |
| WO | WO2012018991 A2 | 2/2012 |
| WO | WO2012/118907 A2 | 9/2012 |
| WO | WO2012118962 A2 | 9/2012 |
| WO | WO2012/154278 A1 | 11/2012 |
| WO | WO2013/020092 A1 | 2/2013 |
| WO | WO2013/059678 A1 | 4/2013 |
| WO | WO2013/162471 A1 | 10/2013 |
| WO | WO2013/165689 A1 | 11/2013 |
| WO | WO2013165614 A1 | 11/2013 |
| WO | WO2014/074573 A1 | 5/2014 |
| WO | WO2014/155403 A1 | 10/2014 |
| WO | WO2014/182769 A1 | 11/2014 |
| WO | WO2015/035175 A1 | 3/2015 |
| WO | WO2015/060897 A1 | 4/2015 |
| WO | WO2015/100294 A1 | 7/2015 |
| WO | WO2015/138963 A1 | 9/2015 |
| WO | WO2016/001868 A1 | 1/2016 |

OTHER PUBLICATIONS

American Academy of Ophthalmology; Vision Screening for Infants and Children (Policy Statement); American Association for Pediatric Ophthalmology and Strabismus; 3 pgs; © 2013 (earliest approval date: May 1991).

Cho et al.; Development of real-time dual-display handheld and bench-top hybrid-mode SD-OCTs; Sensors (Basel); 14(2); pp. 2171-2181; Jan. 27, 2014.

Device Optical; Kowa Genesis-D Hand Held Retinal Camera (product information); 3 pgs.; retrieved Jun. 23, 2014 from the internet (http://www.deviceoptical.com/pd_kowa_genesisd.cfm).

Haddock et al; Simple, inexpensive technique for high-quality smartphone fundus photography in human and animal eyes; Journal of Ophthalmology; Hindawi Pub. Corp.; vol. 2013; Art. ID 518479; 5 pgs.; 2013 (accepted Aug. 18, 2013).

Carlo et al.; A review of optical coherence tomography angiography (OCTA); International Journal of Retina and Vitreous; 1(1); 15 pages; Apr. 15, 2015.

(56) References Cited

OTHER PUBLICATIONS

Denny; Pediatric trauma research: Steep rise in kids' eye injuries from air guns; EyeNet magazine; News in Review: commentary and perspectives; American Academy of Opthalmology; pp. 16; Jul. 2015.

Freebody; Reduced to the essentials—portable imaging gets high-tech; BioPhotonics; 13 pages; retrieved Jul. 13, 2016 from the internet at (http://www.photonics.com/Article.aspx?PID=1&VID=127&IID=847&AID=57816).

Ikuno; Macular pathologies and OCT angiography: subteties in the vascular architecture are readily seen on the angioVue imaging system; Optovue; OCT Angiography: The Newest Frontier for the Revolutionary Technology; Euro Times; 2014 supplement; pp. 6-7; Apr. 2014.

Izatt et al.; Theory of optical coherence tomography; Optical Coherence Tomography; Springer berlin Heidelberg; pp. 47-72; (year of pub. sufficiently earlier than effective US filing date and any foreign priority date); 2008.

Karmel; Cataract surgery: Excessive preop testing; EyeNet magazine; News in Review: commentary and perspectives; American Academy of Opthalmology; pp. 17; Jul. 2015.

Ko; The angiovue difference; Optovue; OCT Angiography: The Newest Frontier for the Revolutionary Technology; Euro Times; 2014 supplement; pp. 1-2; Apr. 2014.

Koch; Optovue imaging device offers great potential for anterior segment imaging: The device's ability to image both the anterior and posterior cornea helps provide more accurate IOL calculations, among other things; Optovue; OCT Angiography: The Newest Frontier for the Revolutionary Technology; Euro Times; 2014 supplement; pp. 10-11; Apr. 2014.

Kolb et al.; Ultra-widefield retinal MHz-OCT imaging with up to 100 degrees viewing angle; Biomedical Optics Express; 6(5); pp. 1534-1552; May 2015.

Lumbroso; AngioVue Imaging Syste: The Future of Imaging? After evaluating this system, the answer is mostly likely 'yes'; Optovue; OCT Angiography: The Newest Frontier for the Revolutionary Technology; Euro Times; 2014 supplement; pp. 3-4; Apr. 2014.

Pavlis et al.; Optical differences between telescopes and microscopes; 5 pages; retrieved Jul. 13, 2016 from the internet at (http://www.microscopy-uk.org.uk/mag/imgjan10/mik-tele.pdf).

Puech; Imaging the optic disc with OCCT angiography: New optovue device enhances the way we view glaucoma patients; Optovue; OCT Angiography: The Newest Frontier for the Revolutionary Technology; Euro Times; 2014 supplement; pp. 8-9; Apr. 2014.

Roach; Femtosecond Techniques: The ideal capsulotomy?; EyeNet magazine; News in Review: commentary and perspectives; American Academy of Opthalmology; pp. 17; Jul. 2015.

Roach; New views of retina with OCT angiography; EyeNet magazine; News in Review: commentary and perspectives; American Academy of Opthalmology; pp. 15-16; Jul. 2015.

Ruggeri et al.; Imaging and full-length biometry of the eye during accommodation using spectral domain OCT with an optical switch, Biomedical Optics Express, 3(7); pp. 1506-1520; Jul. 6, 2012.

Staurenghi; Choroidal visualization using a non-invasive microvascular enhanced imaging platform; Optovue; OCT Angiography: The Newest Frontier for the Revolutionary Technology; Euro Times; 2014 supplement; pp. 5-6; Apr. 2014.

Su; U.S. Appl. No. 15/186,402 entitled "Wide field of view optical coherence tomography imaging system," filed Jun. 17, 2016.

Su et al.; U.S. Appl. No. 15/144,679 entitled "Eye imaging apparatus and systems," filed May 2, 2016.

* cited by examiner

DISPOSABLE CAP FOR AN EYE IMAGING APPARATUS AND RELATED METHODS

CROSS REFERENCE TO RELATED APPLICATIONS

This application claims the benefit of U.S. Provisional Application No. 62/107,993, filed Jan. 26, 2015, which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference, including: U.S. Pat. No. 9,155,466, titled "EYE IMAGING APPARATUS WITH A WIDE FIELD OF VIEW AND RELATED METHODS", filed on Feb. 4, 2015, which is a continuation of U.S. application Ser. No. 14/191,291 filed Feb. 26, 2014, which is a continuation-in-part of U.S. Pat. No. 9,179,840, titled "IMAGING AND LIGHTING OPTICS OF A CONTACT EYE CAMERA", filed on Mar. 17, 2013 which claims the benefit of U.S. Provisional Application No. 61/612,306 filed on Mar. 17, 2012, and U.S. patent application Ser. No. 14/220,005, titled "EYE IMAGING APPARATUS AND SYSTEMS", filed on Mar. 19, 2014, which is a continuation-in-part of U.S. application Ser. No. 13/757,798, filed on Feb. 3, 2013, which claims the benefit of U.S. Provisional Application No. 61/593,865, filed on Feb. 2, 2012, and U.S. patent application Ser. No. 14/312,590, titled "MECHANICAL FEATURES OF AN EYE IMAGING APPARATUS", filed on Jun. 23, 2014, and U.S. Provisional Application No. 62/141,209, titled "A WIRELESS IMAGING APPARATUS AND RELATED METHODS", filed on Mar. 31, 2015.

FIELD

Various embodiments of the disclosure relate generally to a disposable cap for a medical imaging apparatus and related methods, and particularly, a disposable cap of a contact eye imaging apparatus and related methods.

BACKGROUND

Medical imaging apparatuses have become increasingly important in medical procedures such as eye examinations and surgeries. For example, an eye imaging apparatus capable of imaging a posterior segment of an eye can be particularly useful in diagnosing retinal and optic nerve problems, which are among the leading causes in vision loss. Compared to a non-contact eye imaging apparatus, a contact eye imaging apparatus has the advantage of a wide field of view which offers the benefit of enabling evaluation of pathologies located on the periphery of the retina. However, the contact eye imaging apparatus has to be placed in direct contact with a cornea of an eye of a patient during the examination, which could potentially cause cross-contamination among patients. Thus, cross-contamination is a concern for a medical imaging apparatus that is in direct contact with patients.

Because a medical imaging apparatus is in general expensive with complex optical systems, it may not be practical to sterilize the imaging apparatus in the autoclave after each use. In addition, the disinfection procedures can be expensive and requires long turn-around time. Furthermore, the traditional disinfecting procedure may not be able to thoroughly eliminate cross-contamination because of the increasing resistance of bacteria and viruses to disinfection. A disposable sterile cover for the medical imaging apparatus is not only cost effective, but also protects the patients from possible cross-contamination resulting from using the imaging apparatus.

However, optical performance is important for a medical imaging apparatus to provide accurate and reliable medical information. Optical performance is particularly important for a contact eye imaging apparatus. As discussed in U.S. application Ser. No. 14/191,291 entitled "Eye Imaging Apparatus with a Wide Field of View and Related Methods", the scattering and reflection from the eye causes significant difficulty in achieving a high quality image of the posterior segment of the eye. For an eye imaging apparatus with an optical window having a concave surface configured to image the posterior segment of the eye, it is important for the disposable cover to conform to the concave shape of the optical window and maintain the concave shape during the attaching and detaching processes in order to obtain the high quality image. Therefore, there is a need for a disposable cap for the eye imaging apparatus that is able to conform to the concave shape of the optical window to achieve high quality optical performance, and to be able to securely attach to and easily detach from the eye imaging apparatus. In addition, a disposable cap has to be able to meet rigorous FDA sterilization requirements and provide an effective physical barrier to bacteria and viruses.

SUMMARY OF THE DISCLOSURE

The present disclosure relates to a disposable cap for an eye imaging apparatus. An eye imaging apparatus with an optical window in direct contact with a cornea of an eye of the patients can potentially cause cross-contamination among patients. A sterile disposable cap can be used to provide a physical barrier between the imaging apparatus and the patients. Before the eye examination or surgery, the disposable cap can be placed onto the frontal portion of the eye imaging apparatus and securely locked with the housing of the eye imaging apparatus. After the medical procedure, the disposable cap can be removed from the housing of the eye imaging apparatus and disposed.

Disclosed herein is a disposable cap for an eye imaging apparatus with an optical window. For example, the eye imaging apparatus can be an eye imaging apparatus described in U.S. Pat. No. 9,155,466, titled "EYE IMAGING APPARATUS WITH A WIDE FIELD OF VIEW AND RELATED METHODS", U.S. patent application Ser. No. 14/220,005, titled "EYE IMAGING APPARATUS AND SYSTEMS", U.S. Provisional Application No. 62/141,209, titled "A WIRELESS IMAGING APPARATUS AND RELATED METHODS", and U.S. patent application Ser. No. 14/312,590, titled "MECHANICAL FEATURES OF AN EYE IMAGING APPARATUS". The disposable cap can be configured to be in contact with an eye of a patient to provide a physical barrier to prevent cross contamination between patients. The disposable cap can have an open end at a proximal end and a covering end at a distal end. In general, the disposable cap can comprise an optically transparent window cover, a distal ridge, a side wall and a locking element comprising a radially inward projection.

In general, the optically transparent window cover can comprise a concave front surface and a convex back surface. The convex back surface can be configured to match a concave shape of a front surface of the optical window of the eye imaging apparatus. The window cover can be made of a material that has certain rigidness and be able to withstand the sterilization process to maintain the shape of the convex back surface. For example, the disposable cap can be made of a thermal plastic material including Polycarbonate (PC). In order to obtain high optical performance, the window cover can have a small thickness. The thickness of the window cover can be between from about 0.01 mm to 3 mm.

The distal ridge of the disposable cap can extend distally and radially outward from the window cover. The distal ridge can be adapted to engage with a corresponding ridge of the eye imaging apparatus to place the window cover against the optical window of the eye imaging apparatus. In one embodiment, the window cover can further comprise a flat, distally facing ring surface extending radially outward from the convex back surface to the distal ridge. In general, the side wall can extend proximally and radially outwardly from the distal ridge toward the open end. The side wall can be adapted to engage with a housing of the eye imaging apparatus. The locking element can comprise one or more radially inward projections and one or more radially outward releasing tabs. The one or more projections can be movably supported with respect to the side wall and configured to attach the disposable cap to the eye imaging apparatus. The one or more releasing tabs can be adapted to detach the disposable cap from the eye imaging apparatus.

In one embodiment, the window cover, the distal ridge, the side wall and the locking element are one-piece formed integrally from a single material. In another embodiment, the window cover, the distal ridge, the side wall and the locking element can be made of same or different materials and be connected together through a variety of manufacturing process such as bonding, welding, and over-molding, etc.

The disposable cap can further comprise a shield extending proximally from the side wall to the locking element and the radially inward projection is movably supported with respect to a side wall of the shield. In one embodiment, the shield can comprise a resilient stretchable material and be connected to the side wall of the window cover. In another embodiment, the shield, the window cover, the distal ridge and the side wall can be made of a same material with certain rigidity to integrally form a one-piece disposable cap. The shield can further comprise a spring style bellow ring, the spring style bellow ring comprising at least one corner.

In one embodiment, the disposable cap can further comprise a sheath proximally and radially outwardly from the shield. The disposable cap can be adapted to cover the entire eye imaging apparatus. In one embodiment, the sheath can be connected to the shield near the projects. The sheath can comprise a resilient stretchable material. In another embodiment, the disposable cap can be an integrally formed one-piece cap comprising the shield, the window cover, the distal ridge and the sheath.

In one embodiment, a length of the disposable cap from the distal end to the projection is slightly shorter than a length of a portion of the imaging apparatus from a distal end to a corresponding locking groove. The disposable cap can initiate engagement with the image apparatus when the convex back surface of the window cover touches the front concave surface of the optical window before a latching action to attach the disposable cap takes place. The latching action elongates the shield of the disposable cap, resulting in a pulling force along the axis of the imaging apparatus which helps to secure the disposable cap to the optical window. The slight deformation of the ridge can absorb most of the movement of the cap at the distal end. The ridge does not only match a contour of a corresponding ridge of the imaging apparatus to reduce air between the disposable cap and the imaging apparatus, but more importantly, helps to prevent the optical window cover from bulging and keep the convex back surface of the disposable cap in shape to precisely match the concave surface of the optical window of the imaging apparatus in order to achieve high quality optical performance. The flat ring surface of the disposable cap can act as an alignment reference to ensure that the convex back surface of the disposable cap precisely matches the concave surface of the optical window of the imaging apparatus. The flat ring can also form a supporting pad for the distal ridge. The distal ridge and the flat ring can work together to prevent the convex back surface of the disposable cap from bulging under the pulling force.

Various embodiments disclosed herein comprise a disposable packaging shell of a disposable cap for an eye imaging apparatus with an optical window. The disposable packaging shell can comprise a sealing lid at a top end. The sealing lid can be adapted to seal the disposable cap from environment before use. The disposable packaging shell can comprise a head extending radially outward at a bottom end. The head can comprise an indentation at a center portion. The indentation can comprise a convex inside surface adapted to match the concave front surface of the window cover of the disposable cap.

The disposable packaging shell can comprise one or more radially inward shell tabs disposed at the top end and open spaces therebetween. The one or more radially inward shell tabs adapted to mate with the one or more radially outward releasing tabs to enable the disposable cap to be attached to and detached from the eye imaging apparatus and to be inserted into and removed from the disposable packaging shell. The disposable cap can be rotational movable with respect to the disposable packaging shell between an open position and a storage position, wherein the one or more radially outward releasing tabs are disposed underneath open spaces in the open position and underneath the one or more radially inward shell tabs in the storage position. In one embodiment, the one or more radially inward shell tabs can have an L-shape comprising a long portion and a short stopper. The long portion can be perpendicular to an optical axis of the imaging apparatus, while the short stopper can be parallel to the optical axis.

In one embodiment, the disposable packaging shell can further comprise a waist which has a diameter smaller than a diameter of the head. The waist can be configured to be held by a user for attaching the disposable cap to and detaching the disposable cap from the eye imaging apparatus. In one embodiment, the disposable packaging shell can further comprise an identifying element containing unique identification information to uniquely identify the disposable cap.

Disclosed herein is also a plug-in disposable system for an eye imaging apparatus with an optical window. The plug-in disposable system can comprise a disposable cap configured to be in contact with an eye of a patient and a disposable packaging shell of the disposable cap. The disposable cap can have an open end at a proximal end and a covering end at a distal end. The disposable cap can comprise an optically transparent window cover comprising a concave front surface and a convex back surface. The convex back surface can be configured to match a concave shape of a front surface of the optical window of the eye imaging apparatus. The disposable cap can comprise a locking element comprising one or more radially inward projections. The one or more projections can be movably supported with respect to the side wall and configured to attach the disposable cap to the eye imaging apparatus. The disposable cap can further comprise one or more radially outward releasing tabs positioned at same locations as the one or more projections and configured to detach the disposable cap from the eye imaging apparatus and to be inserted into and removed from the disposable packaging shell.

The disposable packaging shell of the disposable cap can comprise a sealing lid at a top end. The sealing lid can be adapted to seal the disposable cap from environment before use. The disposable packaging shell can comprise a head extending outward at a bottom end. The head can comprise an indentation at a center portion. The indentation can comprise a convex inside surface adapted to match the concave front surface of the window cover of the disposable cap. The disposable packaging shell can further comprise one or more radially inward shell tabs disposed at the top end and open spaces therebetween. The one or more radially inward shell tabs can be adapted to mate with the one or more radially outward releasing tabs to enable the disposable cap to be attached to and detached from the eye imaging apparatus and to be inserted and removed from the disposable packaging shell. The disposable cap can be rotational movable with respect to the disposable packaging shell between an open position and a storage position, wherein the one or more radially outward releasing tabs are disposed underneath open spaces in the open position and underneath the one or more radially inward shell tabs in the storage position.

Various embodiments of the disclosure comprise a disposable cap for an eye imaging apparatus with an optical window configured to be in contact with an eye of a patient. The disposable cap can comprise an optical window cover. The optical window cover can comprise a concave surface in a central portion and a side wall in a frusto-conical shape. The optical window cover can be configured to match a contour of a front surface of the optical window. The disposable cap can further comprise a locking element configured to lock the disposable cap to the eye imaging apparatus. The disposable cap can be configured to be able to easily attach to and detach from the eye imaging apparatus. In some embodiments, the disposable cap can further comprise a shield connected with the optical window cover. The locking element can be disposed on the shield. In one embodiment, the locking element can comprise one or more locking projections. In another embodiment, the disposable cap can comprise a locking ring. In some embodiments, the disposable cap can further comprise one or more releasing tabs, configured to release the disposable cap from the imaging apparatus. In some embodiment, the shield of the disposable cap can further comprise a spring style structure to allow the flexibility and elongation of the shield during the process of attaching the disposable cap to and detaching the disposable cap from the eye imaging apparatus.

Various embodiments of the disclosure comprise a disposable packaging shell of a disposable cap for an eye imaging apparatus. The eye imaging apparatus can have an optical window configured to be in contact with an eye of a patient. The disposable cap can comprise an optical window cover with a concave surface to match a contour of a front surface of the optical window. The packaging shell can comprise a sealing lid at an open end, a head at a closed end, a concave indentation disposed at the head to support the concave surface of the optical window cover of the disposable cap, one or more shell tabs disposed at the open end and one or more open spaces therebetween. The plurality of shell tabs and open spaces are configured to enable the disposable cap to be attached to and detached from the eye imaging apparatus. In some embodiments, each of the plurality of shell tabs of the packaging shell can comprise a long portion and a short stopper. The short stoppers can be configured to stop the movement of the disposable cap, thus locking the disposable cap to the packaging shell. In some embodiments, the disposable packaging shell can further comprise an identifying element configured to uniquely identify the disposable cap.

Various embodiments of the disclosure comprise a plug-in disposable system for an eye imaging apparatus. The eye imaging apparatus can comprise an optical window configured to be in contact with an eye of a patient and one or more locking grooves. The disposable system can comprise a disposable cap and a disposable packaging shell. The disposable cap can comprise an optical window cover having a concave shape in a central portion configured to match a contour of a front surface of the optical window, and one or more locking projections and releasing tabs. The disposable packaging shell can comprise one or more shell tabs. The disposable cap can be configured to be disposed inside the disposable packaging shell before use and after use. The plurality of the locking projections and locking grooves are configured to lock the disposable cap with the imaging apparatus. The plurality of releasing tabs and the plurality of shell tabs are configured to release the disposable cap from the imaging apparatus.

Various embodiments of the disclosure comprise an eye imaging system. The eye imaging system can comprise an eye imaging apparatus. The eye imaging apparatus can comprise an optical window at a front end of the housing with a concave front surface for receiving the eye, and at least one locking groove. The disposable cap can comprise an optical window cover with a concave surface configured to match a contour of the concave front surface of the optical window, and a locking element configured to lock the disposable cap to the at least one locking groove. The disposable cap can be configured to be able to attach and detach from the eye imaging apparatus.

Various embodiments of the disclosure comprise an eye imaging system with a plug-in disposable sub-system. The eye imaging apparatus can comprise an optical window at a front end of the housing with a concave front surface for the eye, and one or more locking grooves. The disposable sub-system can comprise a disposable cap and a disposable packaging shell. The disposable cap can comprise an optical window cover configured to match a contour of the concave front surface of the optical window, and one or more locking projections and releasing tabs. The disposable packaging shell can comprise one or more shell tabs. The disposable cap can be configured to be disposed inside the disposable packaging shell before use and after use. The plurality of the locking projections and locking grooves are configured to lock the disposable cap with the imaging apparatus. The plurality of releasing tabs and the plurality of shell tabs are configured to release the disposable cap from the imaging apparatus.

Various embodiments disclosed herein comprise a method of preventing cross-contamination caused by an eye imaging apparatus. The eye imaging apparatus can have an optical window configured to be in contact with an eye of a patient and at least one locking groove. The method can comprise disposing an index matching gel to a front surface of the optical window. The method can further comprise attaching a disposable cap to the eye imaging apparatus. The disposable cap can comprise an optical window cover with a concave surface configured to match a contour of the front surface of the optical window and a locking element. The method comprises moving the disposable cap until the locking element and the at least one locking groove mate and lock the disposable cap to the eye imaging apparatus. The method also comprises capturing an image of the eye using the imaging apparatus. The method further comprises detaching the disposable cap from the eye imaging apparatus, and disposing of the disposable cap.

Various embodiments of the disclosure comprise a method of preventing cross-contamination caused by an eye imaging apparatus by using a disposable system. The eye imaging apparatus can comprise an optical window. The optical window can be configured to be in contact with an eye of a patient. The disposable system can comprise a disposable cap and a disposable packaging shell where the disposable cap is disposed inside the disposable packaging shell. The disposable cap can comprise an optical window cover with a concave surface configured to match a contour of the front surface of the optical window. The disposable packaging shell can comprise a sealing lid, a concave indentation configured to support the optical window cover. The method comprises disposing an index matching gel to a front surface of the optical window of the eye imaging apparatus. The method can comprise opening the sealing lid of the disposable packaging shell. The method also comprises placing the disposable packaging shell with the disposable cap over the eye imaging apparatus. The method further comprises moving the disposable packaging shell with the disposable cap to lock the disposable cap to the eye imaging apparatus. The method can comprise pulling the eye imaging apparatus with the disposable cap out of the disposable packaging shell. The method further comprises applying the index matching gel to a cornea of the eye, and contacting the cornea with the disposable cap. The method can comprise capturing an image of the eye by using the eye imaging apparatus. The method further comprises placing the eye imaging apparatus with the disposable cap back into the disposable packaging shell, and moving the disposable packaging shell to lock the disposable cap to the packaging shell. The method can comprise pulling the eye imaging apparatus out of the disposable cap and leaving the disposable cover inside the packaging shell. The method can comprise disposing of the disposable packaging shell with the disposable cap.

In some embodiments, the method of preventing cross-contamination further comprises detecting identification information of the disposable cap before operating the eye imaging apparatus. The identification information can be disposed in an identifying element on the disposable packaging shell.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figures 1A, 1B:
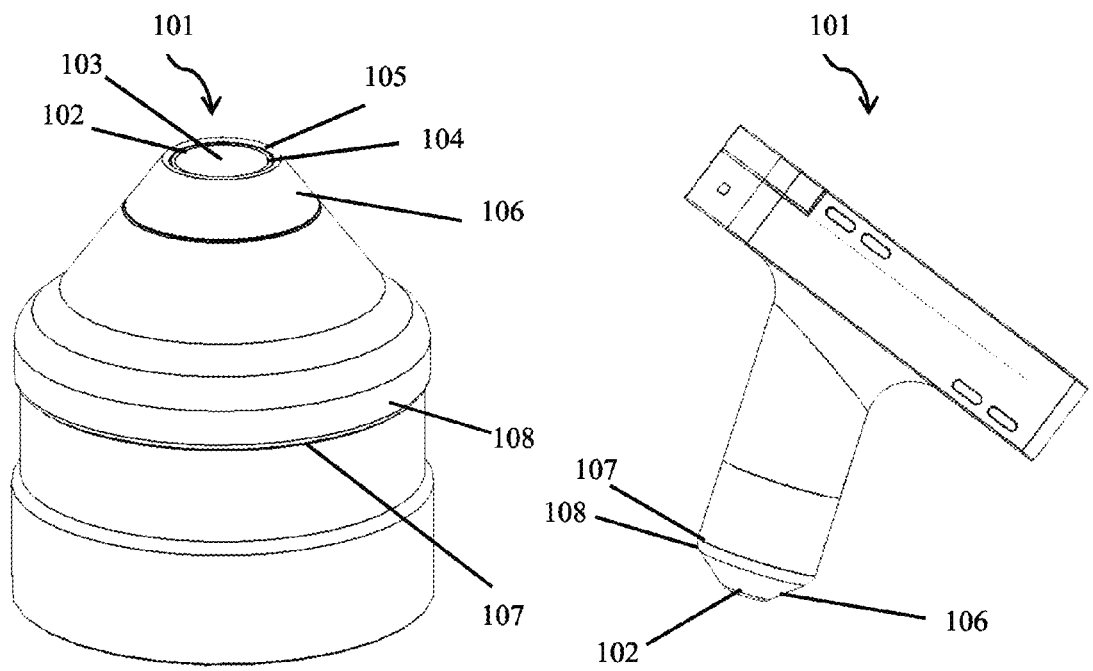
FIG. 1(A) is a perspective view of a distal portion of an eye imaging apparatus.
FIG. 1(B) is a side view of the eye imaging apparatus of FIG. 1(A).

Various aspects of the present disclosure now will be described in detail with reference to the accompanying figures. These aspects of the disclosure may be embodied in many different forms and should not be construed as limited to the exemplary embodiments discussed herein.

Various embodiments of the present disclosure describe a disposable cap for a medical imaging apparatus, for example, an eye imaging apparatus. The disposable cap may be single use and sterile, which can provide a physical barrier between the imaging apparatus and the patients where the imaging apparatus has to be in direct contact with the patients during medical examination or operation. The disposable cap can be manufactured and individually placed into a sealed disposable packaging shell with air-tight sealing in a sterilized environment. The disposable cap can be exposed to Gamma ray or E-beam during the radiation sterilization process or other sterilization processes per FDA requirements. Before use, a sealing lid for the individual sealed packaging shell can be opened and the disposable cap can be attached to the imaging apparatus. The disposable cap can be securely locked to the imaging apparatus. The protective disposable cap can be detached and removed from the imaging apparatus after use. The disposable cap can be single-use and disposed after the medical examination or operation. In another embodiment, the disposable cap can also be used for multiple times after proper sterilization re-processing process.

Disclosed herein is a disposable cap for an eye imaging apparatus with an optical window. The disposable cap can be configured to be in contact with an eye of a patient. In various embodiments, the disposable cap can have an open end at a proximal end of the cap and a covering end at a distal end of the cap. The disposable cap can comprise an optically transparent window cover for the optical window of the eye imaging apparatus. The optically transparent window cover can comprise a concave front surface adapted to be in contact with an eye of the patient and a convex back surface configured to match a concave shape of a front surface of the optical window of the eye imaging apparatus. The disposable cap can comprise a ridge extending distally and radially outward from the window cover. The ridge can be adapted to engage with a corresponding ridge of the eye imaging apparatus to place the window cover against the optical window of the eye imaging apparatus. The disposable cap can comprise a side wall extending proximally and radially outwardly from the ridge toward the open end of the disposable cap. The side wall can be adapted to engage with a housing of the eye imaging apparatus. The disposable cap can comprise a locking element comprising a radially inward projection movably supported with respect to the side wall and configured to attach the disposable cap to the eye imaging apparatus in one embodiment. The disposable cap can further comprise a flat, distally facing surface extending radially outward from the concave surface to the ridge. The disposable cap can further comprise a shield extending proximally from the side wall to the locking element.

The locking element described herein is a broad term including physical structure and texture or any mechanism that are capable of securely attaching the disposable cap to the imaging apparatus. For example, the locking element can comprise a locking groove or one or more locking grooves which matches a locking projection or a plurality of locking projections on the housing of the imaging apparatus in another embodiment. The locking element can comprise an inner surface with certain friction characteristics to prevent the disposable cap from falling off the eye imaging apparatus in another embodiment. The locking element may comprise an outer surface that can be clamped with the housing of the imaging apparatus to secure the disposable cap in yet another embodiment.

Figure 1C:
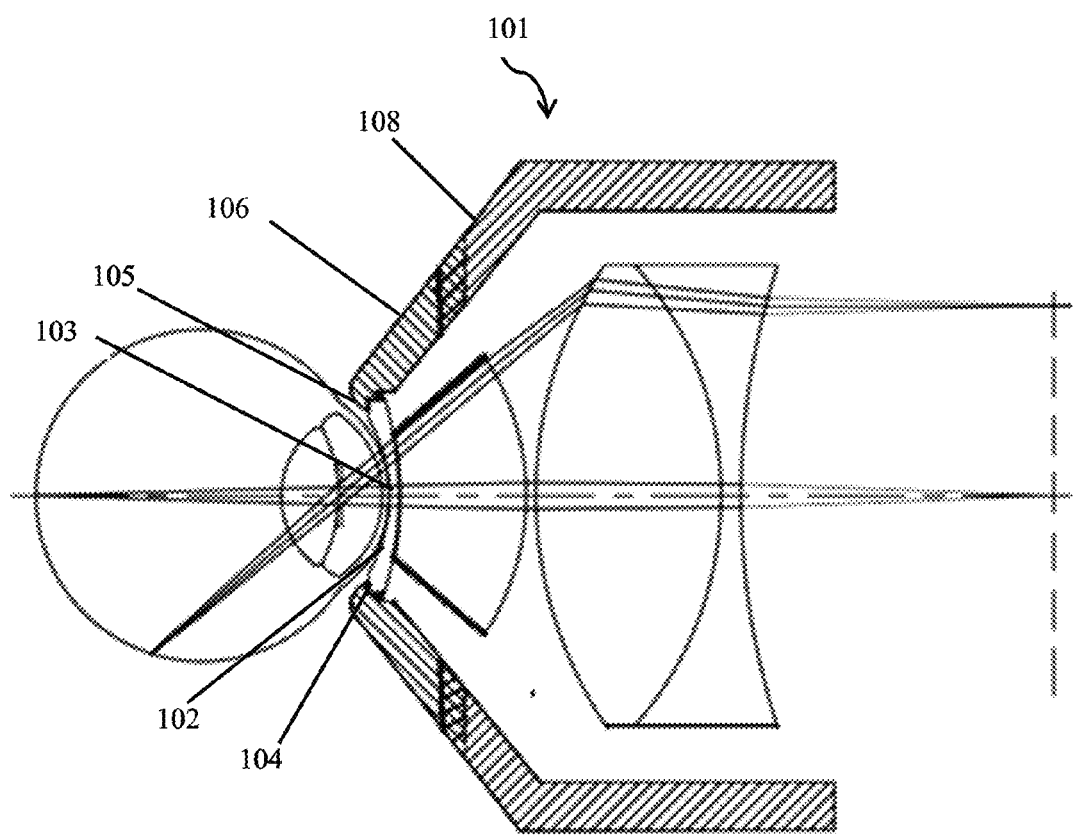
FIG. 1(C) is a cross-section view that schematically illustrates the distal portion of the eye imaging apparatus of FIG. 1(A).

FIG. 1(A) schematically illustrates a perspective view of a distal portion of an eye imaging apparatus 101, FIG. 1(B) schematically illustrates a side view of the eye imaging apparatus 101 and FIG. 1(C) is a cross-section view that schematically illustrates a distal portion of the eye imaging apparatus 101. The details of the eye imaging apparatus are described in U.S. Pat. No. 9,155,466, titled "EYE IMAGING APPARATUS WITH A WIDE FIELD OF VIEW AND RELATED METHODS", U.S. patent application Ser. No. 14/220,005, titled "EYE IMAGING APPARATUS AND SYSTEMS" and U.S. patent application Ser. No. 14/312, 590, titled "MECHANICAL FEATURES OF AN EYE IMAGING APPARATUS", which are incorporated herein in their entirety.

Referring to FIG. 1A, FIG. 1(B) and FIG. 1(C), the eye imaging apparatus 101 can comprise an optical window 102 at a distal end of a window housing 106 of the imaging apparatus 101. For example, an eye imaging apparatus 101 can have an optical window 102 configured to be in contact with a cornea of an eye of a patient, as disclosed in U.S. Pat. No. 9,155,466. In use, the optical window 102 may be placed in contact with the cornea of the eye with slight pressure to obtain a wide field of the view of the retina through the pupil. Accordingly, the optical window 102 may have a concave surface 103 with a radius of curvature closely matching a curvature of the cornea of the eye. In some embodiments, for example, the outer surface of the optical window 102 has a radius of curvature of between 6 mm and 15 mm.

The optical window 102 is optically transparent and can comprise materials such as optical glass. The frontal surface of the optical window 102 can comprise the concave surface 103 and a small flat ring 104 surrounding the concave surface 103. All of the surfaces can be optically polished. The window housing 106 of the eye imaging apparatus 101 can comprise metal or other materials. The distal end of the window housing 106 extends around the edge of the optical window 102. The distal end of the window housing 106 has a smooth ridge 105 to prevent injury to the patients during the operation and to protect the optical window 102 from scratching by hard foreign objects. The small flat surface 104, in the form of a circular ring, may be disposed on the front peripheral area of the optical window 102. This small flat ring 104 may be near and/or extend from the side of the optical window 102 to or near to the edge of the front concave surface 103 of the optical window 102.

The optical window 102 can enable light to enter into and exit out of the window housing 106. Since the eye is a complicated biological organ with its own special optical systems, the scattering and reflection of light from the eye in combination with its small aperture cause significant difficulties in obtaining a high quality image. In particular, the reflection and scattering of light from the eye causes glare and haze, which obscures the images acquired by an eye imaging apparatus. Thus the images from the posterior segment of the eye with a wide field of view often exhibit a layer of strong haze or glare. This problem is especially acute with patients who have dark pigmentation in their eyes. Providing illumination through certain regions of the eye, however, can reduce this backscatter and reflection and the resultant haze and glare. In order to obtain high quality images of the posterior segment of the eye, the eye imaging apparatus 101 can further comprise a light conditioning element configured to receive light from the light source and direct light to the eye to provide desired illumination.

In some embodiments, the housing of the imaging apparatus can comprises a distal section, which is the window housing 106, and a proximal section, which is the apparatus housing 108. The apparatus housing 108 can comprise metal or other materials. The window housing 106, which may be a small housing, can comprise the same or different metal material, in some embodiments, is connected to the apparatus housing 108 by a bond. When the window housing 106 is aligned with the apparatus housing 108, then the optical window 102, may, for example, be properly aligned with the optical axis of the imaging lens and imaging system.

Referring back to FIGS. 1(A) and 1(B), the imaging apparatus 101 may further comprises at least one locking groove 107 which can be configured to mate with a locking element of a disposable cap in some embodiments. For example, the locking groove or locking grooves 107 can be disposed on an apparatus housing 108 of the imaging apparatus 101. In some other embodiments, the imaging apparatus may further comprises at least one locking ridge which can be configured to mate with a locking element of the disposable cap.

Figure 2A:
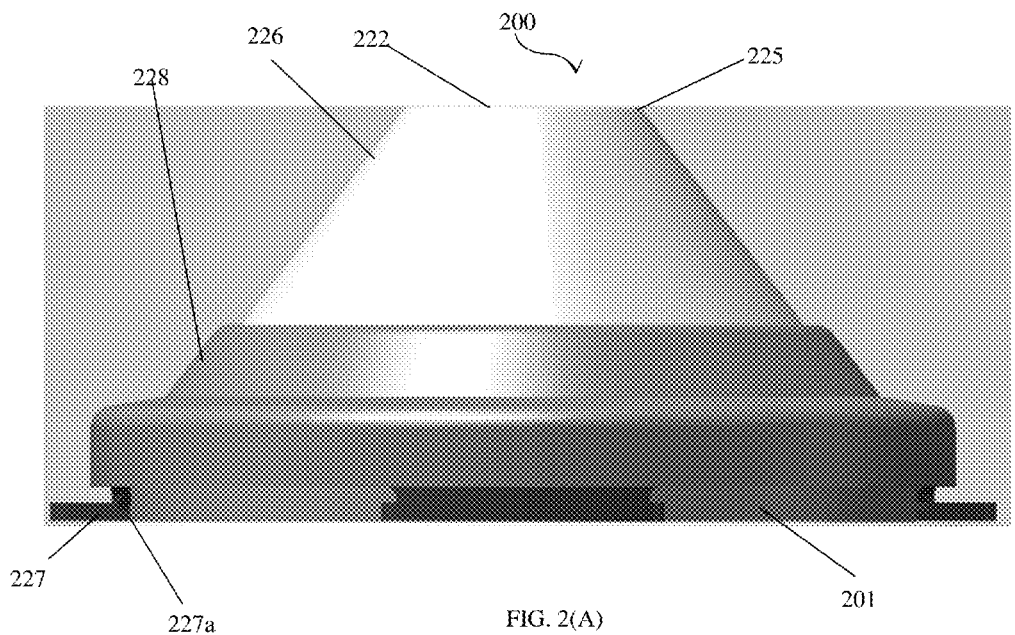
FIG. 2(A) is a side view of a disposable cap placed over an eye imaging apparatus according to one embodiment of the present disclosure.
Figure 2B:
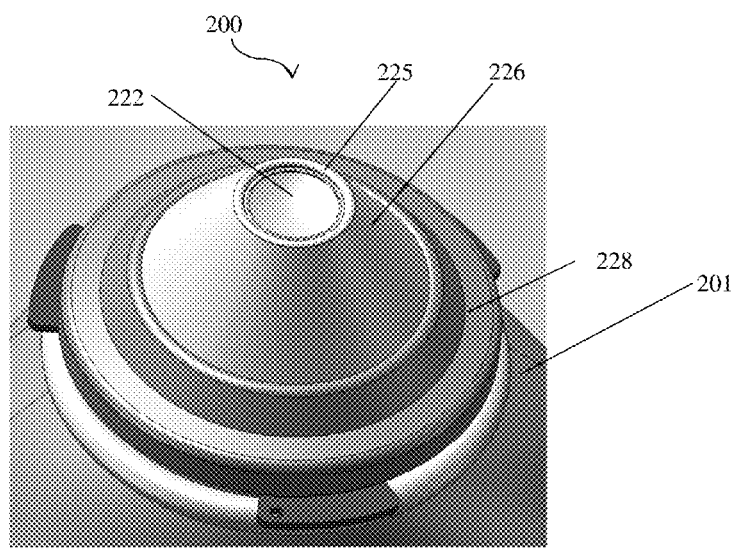
FIG. 2(B) is a perspective view of the disposable cap of FIG. 2(A).

FIG. 2(A) is a side view that schematically illustrates a disposable cap 200 placed over an eye imaging apparatus 201 according to one embodiment of the disclosure. FIG. 2(B) is a perspective view that schematically illustrates the disposable cap 200 placed over the eye imaging apparatus 201. Referring to FIGS. 2(A)-(B), the disposable cap 200 can comprise a window cover 222, a distal ridge 225, a side wall 226 and a locking element 227. As discussed above, the scattering and reflection from the eye in combination with its small aperture cause significant difficulties in obtaining a high quality image of the eye. One side of the optical window cover 222 of the disposable cap 200 can be specially configured to match an exterior contour of the optical window of the imaging apparatus 201, and the other side of the optical window cover 222 can be configured to match the contour of the patient's cornea, to provide high optical performance. The disposable cap 200 can have an open end at a proximal end of the cap 200 and a covering end at a distal end of the cap 200.

As shown in FIG. 2(A) and FIG. 2(B), the disposable cap 200 can comprise the distal ridge 225. The ridge 225 can extend distally and radially outward from the window cover 222. The ridge 225 can be adapted to engage with a corresponding ridge of the eye imaging apparatus 201 to place the window cover 222 against the optical window of the eye imaging apparatus 201. As a result, the ridge 225 can have a shape and a size matching a shape and a size of the corresponding ridge of the window housing of the eye imaging apparatus 201. The ridge 225 does not only act to match the corresponding ridge of the eye imaging apparatus 201 to prevent air bubbles from being trapped between the disposable cap 200 and the imaging apparatus 201, but also plays important role in keeping the optical window cover 222 in a concave shape. In order to obtain high quality images, the optical window cover 222 has to have a small thickness. The thickness of the optical window cover 222 can be between about 0.01 mm to about 3 mm. Values outside the above range are also possible. When the disposable cap 200 is being attached to the imaging apparatus 201, a pulling force can be applied to the window cover 222. Because of the small thickness of the window cover 222, the pulling force can make the window cover 222 bulge, turning from the concave shape to a convex shape, if there is no ridge 225. However, because of the existence of the ridge 225, most of the pulling force can be absorbed by engagement of the ridge 225 with the corresponding ridge on the eye imaging apparatus, thus preventing the window cover 222 from bulging and keeping it in the concave shape during the process of attaching the disposable cap 200 to the imaging apparatus 201.

The disposable cap 200 can comprise a side wall 226 as shown in FIGS. 2(A) and 2(B). The side wall 226 can extend proximally and radially outwardly from the ridge 225 toward the open end of the disposable cap 200. The side wall 226 can be adapted to engage with a housing of the eye imaging apparatus 201. The disposable cap 200 can further comprise a locking element 227. The locking element 227 can be configured to securely lock the disposable cover 200 to the imaging apparatus 201. The locking element 227 can comprise a projection 227a, or a plurality of projections 227a. As shown in FIG. 2(A), the one or more projections 227a can be movably supported with respect to the side wall 226 and extend radially inward. The one or more projections 227a can be configured to attach the disposable cap 200 to the eye imaging apparatus 201. For example, the one or more projections 227a can click into a locking groove of the imaging apparatus 201. The one or more projections 227a can latch the disposable cap 200 to the imaging apparatus 201.

In one embodiment, the disposable cap 200 can be constructed with the optical window cover 222 and the locking element 227 as a single integral piece. The optical window cover 222 and the locking element 227 can comprise the same material. The locking element 227 can be disposed on the optical window cover 222 directly.

In another embodiment, the disposable cap 200 further comprises a shield 228 that is used to connect the locking element 227 to the optical window cover 222. For example, the shield 228 can be made of a same or different material as the optical window cover 222, and then bonded or glued to the optical window cover 222 in one embodiment. In another embodiment, the shield 228 and the window cover 222 can be one-piece and made from a single integral material. The locking element can be disposed on the shield 228. In another embodiment, the locking element 227 can be made separately with a same or different material as the shield 228, and then bonded or glued to the shield 228. The disposable cap 200 may be attached to eye imaging apparatus 201 by stretching or otherwise radially expanding the locking element 227, slipping the cap 200 over the eye imaging apparatus 201 so that the optical window 222 lines up with the optical window of eye imaging apparatus 201, then permitting the locking element 227 to radially contract to grip the housing of the eye imaging apparatus 101. For example, the one or more radially inward projections 227a can be movably supported with respect to a side wall of the shield 228 and configured to attach the disposable cap 200 to the eye imaging apparatus 201.

Figure 3A:
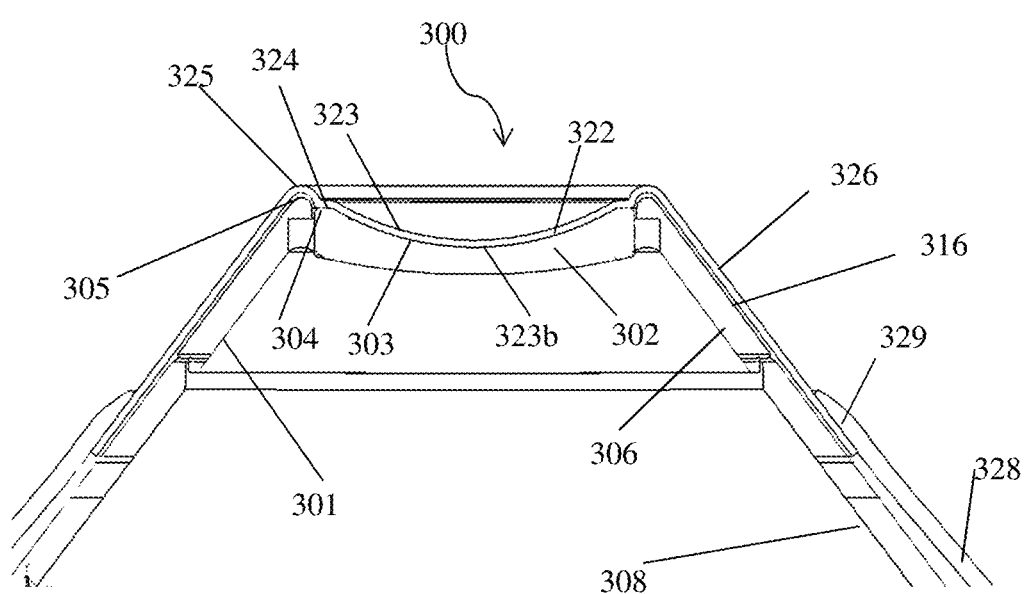
FIG. 3(A) is a cross-sectional view of a portion of a disposable cap according to an embodiment of the present disclosure disposed over an eye imaging apparatus.

FIG. 3(A) schematically illustrates a section view of the disposable cap 300 disposed over an eye imaging apparatus 301. Unless otherwise noted, reference numerals used in FIGS. 3(A)-(H) represent components similar to those illustrated in FIG. 2(A)-(B), with the reference numerals incremented by 100. The disposable cap 300 can be a single-use cap and be disposed after each use. The disposable cap 300 can comprise an optical window cover 322 which may be a rigid, thin and optically transparent material as discussed above. The disposable cap 300 can be configured to cover the optical window 302 and the window housing 306 of the imaging apparatus 301. The frontal surface of the optical window 302 of the eye imaging apparatus can comprise a concave surface 303 and a small flat ring 304 surrounding the concave surface 303. The optical window cover 322 can comprise a concave front surface 323 and a convex back surface 323b. The convex back surface 323b can be configured to precisely match the concave surface 303 of the optical window 302 of the eye imaging apparatus 301 such that the optical window cover 322 and the optical window 302 can be fit together with no air space, or minimum amount of air space therebetween. The optical window cover 322 may also comprise a flat ring portion 324 surrounding the concave surface 323 to fit the flat ring 304 of the optical window 302 of the eye imaging apparatus.

As shown in FIG. 3(A), the optical window cover 322 of disposable cap 300 can comprise the concave front surface 323 and a convex back surface 323b in a central portion. The optical window cover 322 can have a closed covering end at a distal end and an open end at a proximal end where the closed distal end has a smaller diameter than the open proximal end. As discussed above, there are significant difficulties in obtaining a high quality image of the posterior segment of the eye because of the scattering and reflection from the eye in combination with the small aperture of the eye. Providing the optical window cover 322 with the back convex surface 323b that matches with the contour of the front surface 303 of the optical window 302 of the eye imaging apparatus 301 allows the imaging apparatus 301 to achieve high optical performance. The optical window cover 322 can comprise an optically transparent material. By selecting optically transparent material(s) for the optical window cover 322 that have a small birefringence, aberration of the images transmitted therethrough can be minimized. The material can also provide a physical barrier preventing all of virus and bacteria from penetrating the optical window cover 322 when the cover 322 is made with minimum thickness and exposed for at least 2 hours.

The optical window cover 322 can have the back convex surface 323b in a central portion with a curvature configured to closely match the curvature of the concave surface 303 of the optical window 302, as well as the flat ring 324 at the edge to match with the small flat ring area 304 of the optical window 302. Therefore the optical window cover 322 and the optical window 302 can have a tight fit which can minimize scattering, reflections and diffractions from an interface of the optical window cover 322 and the optical window 302. For example, the back convex surface 323b of the optical window cover 322 can be configured to have the same curvature as the curvature of the front concave surface 303 of the optical window 302 at the center portion. The flat ring 324 of the optical window cover 322 can also be configured to have a tight fit with the optical window 302 over the flat ring surface 304. The optical window cover 322 can comprise a rigid shape that precisely matches the contour of the front surface of the optical window 302 and the window housing 306 of the imaging apparatus 301.

The thickness of the optical window cover 322 may have to be small enough to obtain the high quality image of the eye. However, the thickness of optical window cover 322 may have to be large enough to have sufficient rigidness in order to maintain the front concave surface 323 and the back convex surface 323b in shape during the processes of attaching the disposable cap 300 to and detaching the disposable cap 300 from the imaging apparatus 301. Otherwise, undesirable deterioration of the quality of the images of the eye may occur. In some embodiments, the thickness of the optical window cover 322 can be 0.01 mm, 0.1 mm, 0.15 mm, 0.2 mm, 0.25 mm, 3 mm or any values therebetween. The thickness of the optical window cover 322 can be outside the above range as well. The thickness of the optical window cover 322 can also vary at different areas of the cover 322. The curvature of the optical window cover 322 can be configured to closely match the curvature of the optical window 302. In some embodiments, for example, the optical window cover can have a radius of curvature of between 6 mm and 15 mm. The radius of curvature of the optical window cover 322 can be outside the above range as well. The diameter of concave surface 323 of the optical window cover 322 depends on the diameter of the optical window 302 of the eye imaging apparatus 301 it is intended to cover. In some embodiments, for example, the diameter of the front concave surface 323 and the back convex surface 323b of the optical window cover 322 can be 4 mm, 5 mm, 10 mm, 20 mm, or any values therebetween. The diameter of the concave surface 323 and the back convex surface 323b of the optical window cover 322 can be outside the above range as well. The height of the optical window cover 322 can be related to the manufacturing process. In some embodiments, the height of the optical window cover 322 can be 10 mm, 20 mm, 30 mm or any values therebetween. The height of the optical window cover 322 can be outside the above range as well. The diameter of the open end of the optical window cover 322 depends on the height of the optical window. In some embodiments, for example, the diameter of the open end of the optical window cover 322 can be 10 mm, 20 mm, 30 mm, 40 mm or any values therebetween. The diameter of the open end of the optical window cover 322 can be outside the above range as well.

The disposable cap 300 can comprise a distal ridge 325, which extends distally and radially outwardly from the flat ring portion 324. The distal ridge 325 can match a size and shape of the ridge 305 of the imaging apparatus 301. The ridge 325 can be an elevated smooth surface extending distally and radially outward from the window cover 322. The cross section of the ridge 325 can be a smooth surface in a shape of circular, elliptical, parabolic or other smooth surface following a contour of the corresponding ridge 305 of the imaging apparatus 301.

The disposable cap 300 can further comprise a side wall section 326 extending proximally and radially outwardly from the ridge 325 toward an open end of the disposable cap 300. The side wall 326 can be adapted to engage with the window housing 306 of the eye imaging apparatus 301. The sidewall 326 can have a frusto-conical shape, which is a truncated conical shape that conforms to a contour of the window housing 306 of the imaging apparatus 301. The distal ridge 325 and the side wall 326 may be integral with the optical window cover 322 and the flat ring portion 324 and therefore made from the same rigid, optically clear material. The shapes of these elements can follow the contour of the distal ridge 305 of the eye imaging apparatus 301 and the window housing 306 of the eye imaging apparatus 301 with only a small air space 316 between the side wall 326 and the exterior surface of the window housing 306. The small air space 316 (ranged from 0.01 mm and 1.0 mm) is reserved such that the optical window cover 322 can be moved slightly in order to precisely align with the optical window 302. When the disposable cap 300 is being attached to the imaging apparatus 301, a force can push the window cover 322 to align with the optical window 302 through the convex back surface 323b and the flat ring surface 324. Since there can be a small de-centering between the optical window 302 and the window housing 306, the small air space 316 can allow a small adjustment of the window cover 322 in order to precisely align the window cover 322 with the optical window 302.

The thickness of the disposable cap 300 could vary from one part to another, or to be uniform across the whole device. The thickness of the optical window cover 322 may be from about 0.01 mm to about 3.0 mm. The diameter of the optical window cover 322 is from about 5 mm to about 15 mm. Values outside the above ranges are also possible.

Figure 3B:
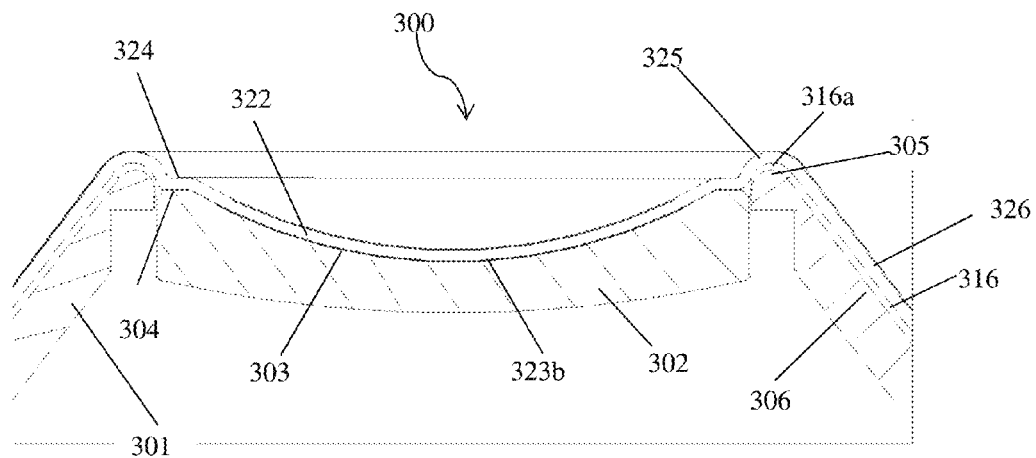
FIG. 3(B) is a cross-sectional view of a distal portion of the disposable cap of FIG. 3(A) after the disposable cap is placed over the imaging apparatus but before being attached to the imaging apparatus.
Figure 3C:
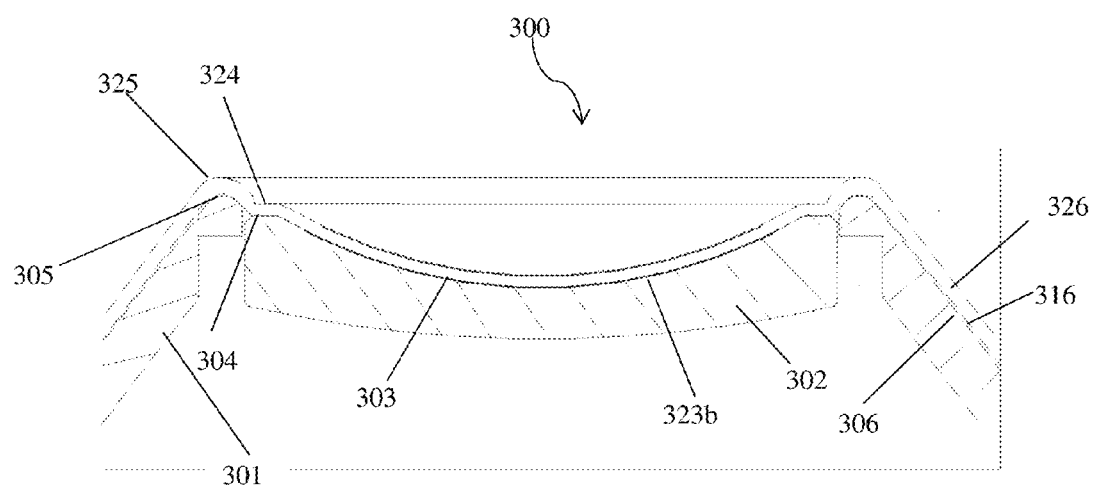
FIG. 3(C) is a cross-sectional view of the distal portion of the disposable cap of FIG. 3(A) after being attached to the imaging apparatus.
Figure 3D:
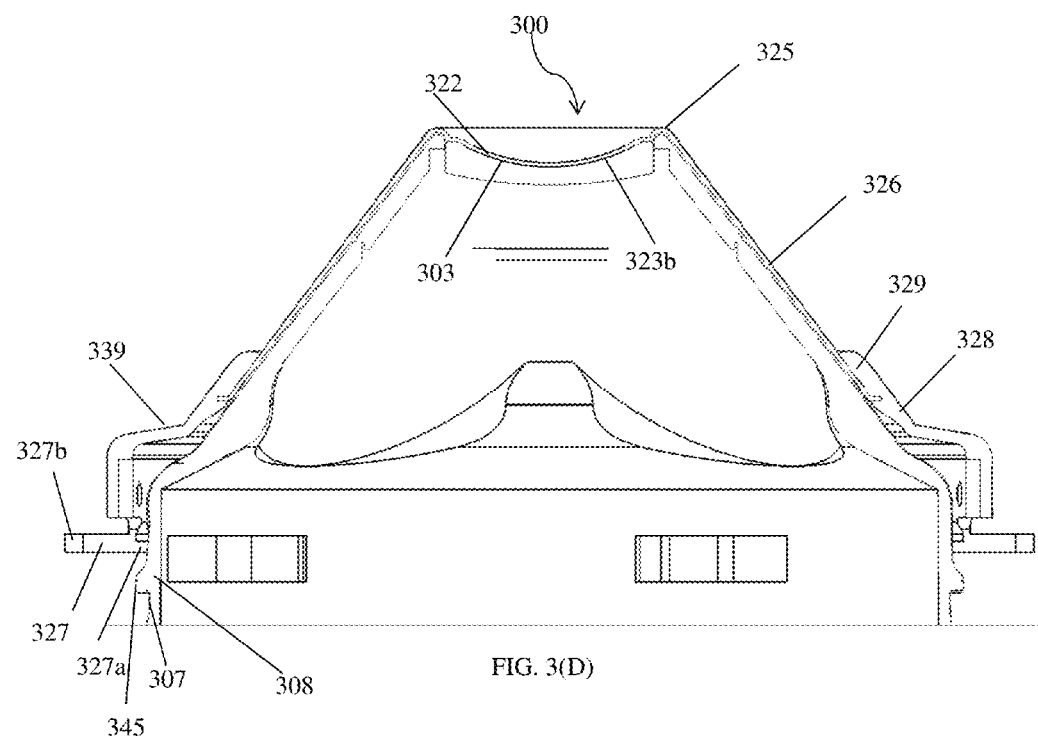
FIG. 3(D) is a cross-sectional view of the disposable cap of FIG. 3(A) after the disposable cap is placed over the imaging apparatus but before being attached to the imaging apparatus.
Figure 3E:
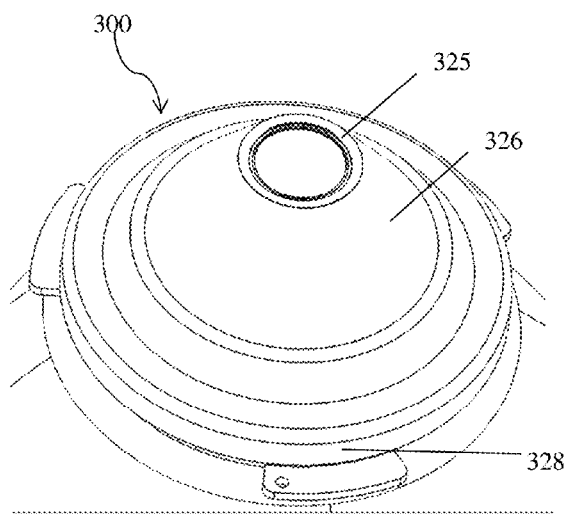
FIG. 3(E) is a perspective view of the disposable cap of FIG. 3(A) being placed over the imaging apparatus.
Figure 3F:
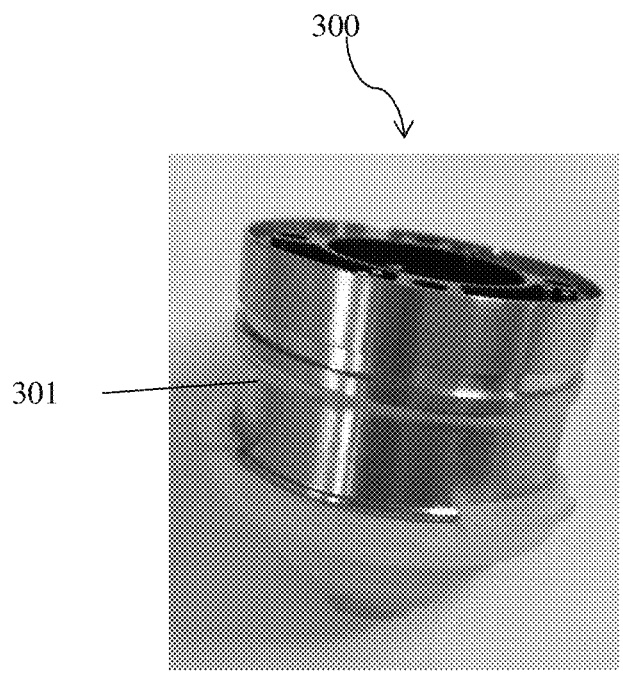
FIG. 3(F) is a photo of the disposable cap disposed over the eye imaging apparatus.
Figure 3G:
FIG. 3(G) is a photo of the disposable cap and the eye imaging apparatus.

FIG. 3(B) is a close section view of a distal portion of the disposable cap 300 after the disposable cap 300 is placed over the imaging apparatus 301 before a latching action to attach the disposable cap 300 to the imaging apparatus 301. FIG. 3(C) is a close section view of the distal portion of the disposable cap 300 after the latching action to lock the disposable cap 300 to the imaging apparatus 301. FIG. 3(D) is a section view of the disposable cap 300 after the disposable cap 300 is place over the imaging apparatus 301 before the latching action to attach the disposable cap 300 to the imaging apparatus 301. FIG. 3(E) is a perspective view of the disposable cap 300. FIG. 3(F) and FIG. 3(G) are photos of a distal end of the eye imaging apparatus 301 covered by a disposable cap 300 and uncovered by a disposable cap 300, respectively. Referring to FIGS. 3(A)-(G), the disposable cap 300 can further comprise a shield 328 and a locking element comprising one or more projections 327a. The one or more projections 327a can be radially inward and movably supported with respect to a side wall of the shield 328. The one or more projections 327a can be latched to a corresponding locking groove 307 of the imaging apparatus 301, thus attaching the disposable cap 300 to the eye imaging apparatus 301.

As shown in FIG. 3(B), in use, the disposable cap 300 can be placed over the imaging apparatus 301, or the imaging apparatus 301 can be inserted into the disposable cap 300 until the convex back surface 323b of the window cover 322 of the disposable cap 300 engages the front concave surface 303 of the optical window 302 of the eye imaging apparatus 301. A small air space or gap 316a can exist between a back surface of the distal ridge 325 of the disposable cap 300 and a front surface of the ridge 305 of the imaging apparatus 301 as shown in FIG. 3(B). The latching action can be applied through a projection 327a of locking element of the disposable cap 300 to pull the sidewall 326 of the disposable cap 300 from the ridge 325 towards the open end of the disposable cap 300 until the projection 327a latches with the locking groove 307 of the imaging apparatus 300 and attaches the disposable cap 300 to the imaging apparatus 301. After the latching action, the disposable cap 300 can be attached to the imaging apparatus 301. The small air space or gap 316a between the back surface of the distal ridge 325 of the disposable cap 300 and the front surface of the ridge 305 of the imaging apparatus 301 can disappear or be essentially eliminated as shown in FIG. 3(C). The distal ridge 325 of the disposable cap 300 can engage the ridge 305 of the imaging apparatus 301. The air space 316 between the side wall 326 of the disposable cap 300 and a side wall of the window housing 306 of the imaging apparatus 301 can be reduced after the latching action as shown in FIG. 3(B) and FIG. 3(C). The air space 316 is reserved after the latching action to precisely align the window cover 322 to the optical window 302 because there may be a slight de-centering between the optical window 302 and the window housing 306.

In one embodiment, a length of the disposable cap 300 from the distal end to the projection 327a can be slightly shorter than a length of a portion of the imaging apparatus 301 from a distal end to the corresponding locking groove 307. The disposable cap 300 can initiate engagement with the image apparatus 301 (more precisely the optical window 302) when the convex back surface 323b of the window cover 322 touches the front concave surface 303 of the optical window 302 before the latching action takes place. The latching action elongates the shield 328 of the disposable cap 300, resulting in a pulling force along the axis of the imaging apparatus 301 which helps to secure the disposable cap 300 to the optical window 302. Such pulling force can help to ensure that the cap 300 stays with optical window 302.

Referring to FIGS. 3(B) and 3(C), the pulling or stretching force can be applied to the disposable cap 300 towards the open end of the disposable cap 300 during the latching action. If the pulling force applies directly on the window cover 322, the window cover 322 may bulge because of its small thickness. The convex back surface 323b may become a concave surface and air bubbles may be trapped between the disposable cap 300 and the imaging apparatus 301. The back convex surface 323b of the disposable cap 300 may not be able to fit the concave front surface 303 of the optical window 302 precisely. The optical quality of the imaging apparatus 301 may be compromised. The distal ridge 325 acts as a buffer of the pulling force since most of the pulling force applies to the distal ridge 325. The slight deformation of the ridge 325 absorbs most of the movement of the cap 300 at the distal end. The ridge 325 does not only match a contour of a corresponding ridge 305 of the imaging apparatus 301 to reduce air between the disposable cap 300 and the imaging apparatus 301, but more importantly, helps to prevent the optical window cover 322 from bulging and keep the convex back surface 323b of the disposable cap 300 in shape to precisely match the concave surface 303 of the optical window 302 of the imaging apparatus 301 in order to achieve high quality optical performance.

The flat ring surface 324 of the disposable cap 300 can act as an alignment reference to match the flat ring 304 of the imaging apparatus 301. Therefore the flat ring 324 can act as an alignment reference to ensure that the convex back surface 323b of the disposable cap 300 precisely matches the concave surface 303 of the optical window 302 of the imaging apparatus 301. The flat ring 304 can also form a supporting pad for the distal ridge 325. When the disposable cap 300 is latched, the pulling or stretching force pulls the disposable cap 300 closer to fit tightly with the exterior of the window housing 306, the slight deformation of the ridge 325 absorbs most of the movement of the cap 300 at the distal end while transferring a small portion of the pulling force to the flat ring 304 which helps keeping the back convex surface 323b of the optical window cover 322 in shape. At the distal end, most of the pulling force is transferred to the window housing 306 through the surface contact at the ridge 325, which resolves the problem that such pulling force may not be able to be precisely controlled in practice while the impact of such pulling force on the convex back surface 323b has to be minimized in order to obtain high optical performance. The distal ridge 325 and the flat ring 324 of the disposable cap 300 work together to prevent the convex back surface 323b of the disposable cap 300 from bulging under the pulling force.

The optical window 302 may need to be precisely aligned with the window housing 306. The gap between the optical window 302 and the window housing 306 may have to be small and uniform. The optical window 302 and the window housing 306 may have a symmetric shape. In one embodiment, the optical window cover can have a uniform thickness. In another embodiment, the thickness of the optical window cover 322 can be slightly different from one section to another.

The optical window cover can be configured to use in various medical imaging applications. The optical window cover can comprise shapes other than a concave front surface and a convex back surface and be suitable for optical windows with different shapes. For example, the optical window cover can have a concave surface, a convex surface, a spherical surface, a non-spherical surface, or any other different shape of surface, or a combination of different surfaces that matches the contour of the front surface of the optical window in different medical applications.

The optical window cover 322 can comprise a variety of materials including plastic, glass, polymer or any other materials that can satisfy the optical quality requirements discussed above. In some embodiments, the optical window cover 322 can comprise optical transparent materials with low birefringence. In some embodiments, the optical window cover 322 can be made of thermal plastic materials, for example, polyethylene terephthalate (PET, PETE, PETG) or polymethyl methacrylate (PMMA), Polycarbonate (PC), Acrylonitrile butadiene styrene (ABS), Polybenzimidazole (PBI), Polyethylene (or polyethene, polythene, PE), Polypropylene (PP), Polystyrene, Polyvinyl chloride (PVC), Teflon, etc.

In one embodiment, the optical window cover 322 can be manufactured through thermoforming process. For example, the optical window cover 322 can be formed through vacuum forming process which is one type of thermoforming. Vacuum forming process has a low operating temperature which results in small birefringence. The relatively fast forming cycles of the vacuum forming process can also have the advantages of high efficiency and low cost. In another embodiment, the optical window cover 322 can be manufactured through injection molding process. Yet in some alternative embodiment, the optical window cover 322 can be manufactured through other thermoforming process. In another alternative embodiment, the optical window cover 322 can be manufactured through other non-thermal process.

The optical window cover 322 can be made of materials which satisfy the sterilization requirements. The optical window cover 322 should be capable of providing an effective physical barrier from bacteria and viruses. The optical window cover 322 should be bio-compatible without harmful and toxic materials to human beings. The optical window cover can comprise bio-degradable materials. The optical window cover 322 can be made of materials that prevent penetration of liquid and gas from outside into its interior space for certain period of time, for example, 1 hour or more, or permanently. The optical window cover 322 can be made of materials that are capable of withstand radiation dosage required from the Gamma and E-beam sterilization process, and the environment in high temperature/high moisture autoclaving operations.

The optical window cover 322 can be made of materials that are capable of withstanding Gamma Ray and Electron Beam (E-beam) sterilization. Gamma ray and E-beam sterilization has the advantages of reduced post-sterile release cycle time in addition to no toxic chemical substances. The optical window cover 322 can comprise a variety of materials that can withstand Gamma ray or E-beam radiation. For example, the optical window cover 322 can be made of thermal plastics materials that exhibit good stability after Gamma ray sterilization such as Acrylonitrile/Butadiene/Styrene (ABS), aromatic polyesters (PET, PETG), polyvinyl fluoride, polyvinylidene fluoride, Ethylene-Tetrafluoroethylene (ETFE), polyallomers, polyamides alphatic, polyamides aromatic, polycarbonate, polyethylene, poly (ethylene-acrylate), polyimides, polymethylpentene, polyphenylene sulfide, polystyrene, polysulfone, polyvinyl formal, polyvinylbutyral, polyvinylchloride (PVC), polyvinylidene Chloride, Styrene/Acrylonitrile (SAN), Allyl digylcol carbonate (polyester), polymethylpentene, Polyphenylene Sulfide, etc.

The optical window cover 322 can comprise materials with a hydrophilic surface or a hydrophobic surface. For a wide field of view optical imaging system, an optical index matching gel or liquid can be used to help to eliminate a significant amount of optical aberrations originated from the cornea of the eye. The optical index matching gel can be applied between the optical window 302 of the eye imaging instrument and the optical window cover 322, and/or between the optical window cover 322 and the cornea of the eye. A hydrophilic surface of the optical window cover 322 can prevent air bubbles from being trapped near the optical window cover 322. The trapped air bubbles can reduce the quality of the images. If the material is hydrophobic, a hydrophilic coating could be applied to the surfaces of the optical window cover 322. In another embodiment, the surfaces could remain hydrophobic. During the eye examination, an optical index matching liquid or gel, both of which are optically clear and with index of refraction equal or larger than that of water, can be disposed between the curved surfaces of the optical window cover 322 and the optical window 302. The optical index matching liquid or gel can also be disposed between the optical window cover 322 and the cornea of the eye. Such liquid or gel can be used to squeeze out the air between the optical window cover 322 and the optical window 302, and between the optical window cover 322 and the cornea of the eye, thus reducing optical scatterings. The index matching liquid or gel can be water based or oil based. In some embodiments, the optical index matching liquid or gel is applied directly to the patient's eye, applied to the exterior (distal side) of the optical window cover 322, and/or applied directly to the optical window 302 of the imaging apparatus at one or more times during the medical examination or operation.

In one embodiment, the back convex surface 323b of the optical window cover 322 can be coated with a thin adhesive coating to enhance the bonding between the optical window cover 322 and the optical window 302. The thin adhesive coating can also act as an optical index matching material as well. However, such adhesive coating is not configured to be used for permanent bonding with strong adhesive force. The optical window cover 322 is configured to be easily removed from the optical window 302 and the housing 306 after the medical examination or operation. In another embodiment, the adhesive coating on the interior side (i.e. convex side) of concave surface 323 of the optical window cover 322 can be hydrophilic and only exhibits the adhesive characteristic after water or water based gel is applied to the surface of the optical window cover 322. A special coating may be applied to the interior surface of the optical window cover 322, before the adhesive coating is added, to enhance the bonding between the optical window cover 322 and the optical window 302.

Referring to FIGS. 3(A)-3(E), the single-use, sterile disposable cap 300 can further comprise the shield 328. The shield 328 can have a small overlapping area 329 over the optical window cover 322. The clear optical window cover 322 and the shield 328 can be connected together at the joint section of the overlapping area 329. The clear optical window cover 322 and the shield 328 can be joined by various processes such as bonding, gluing, over-molding or other manufacturing processes.

The shield 328 can be disposed around the apparatus housing 308. The shield 328 may comprise a variety of materials such as Thermoplastic Elastomer (TPE), rubber, plastic, polymer or any other materials that can withstand Gamma ray or E-beam radiation and have certain flexibility and elasticity. The shield 328 can comprise elastic or flexible materials such as rubber, or rubber like materials. For example, the shield 328 can comprise thin wall structure of latex, Vinyl, Nitrile and other elastic materials. The shield 328 may comprise a resiliently stretchable material. The disposable cap 300 may attach to eye imaging apparatus 301 by inserting the eye imaging apparatus into the open proximal end of the disposable cap 300 until the ridge 305 of the eye imaging apparatus 301 engages the ridge 325 of the optical window cover 322 of the disposable cap 300.

In one embodiment, the optical window cover 322 and the shield 328 can be made of two different materials. The optical window cover 322 can comprise a material with certain rigidity that can satisfy both the optical quality requirement and the sterilization requirement. The shield 328 can be made of a material that is resiliently stretchable with certain elasticity. The shield 328 can be connected or bonded to the side wall 326 of the optical window cover 322. During the attaching and detaching process, the elongation of the disposable cap 300 is mostly achieved with the help of elasticity of the material used for the shield 328. The higher elasticity of the material for the shield 328 allows a larger thickness of the shield 328. The thicker wall of the shield 328 may also help to form the bonding between the window cover 322 and the shield 328 though the rubber injection molding process. However, the cost of manufacturing and tooling requirements can be a concern. In addition, it may not be easy to maintain a low rate of failure for the leakage between the joint section of the window cover 322 and the shield 328.

In another embodiment, the disposable cap 300 may further comprises a spring style bellow ring 339 disposed on the shield 328 as shown in FIG. 3(D). For example, the spring style bellow ring 339 may comprise at least one corner. The corner can be about 30 degrees, 60 degrees, 90 degrees, 120 degrees, 150 degrees or any values therebetween. During the attaching process, the disposable cap 300 may be extended to a larger length along the optical axis direction of the imaging apparatus 301 than the length of the disposable cap 300 in the locking position to allow the open proximal end of the disposable cap 300 to pass a locking ridge 345 in the apparatus housing 308. The spring style bellow ring 339 can be configured to allow the disposable cap 300 to be inserted over the locking groove 307. Once the locking projection or projections 327a is locked into the locking groove 307 of the apparatus housing 308, the disposable cap 300 can return to the normal length with nominal elongation of the shield 328. The spring style bellow ring 339 is configured to allow the flexibility of the disposable cap 300 along the optical axis direction during the attaching process and extra elongation of the shield 328 when the one or more projections 327a are in the locking position. By using the spring style bellow ring 339, the optical window cover 322 and the shield 328 can be made of the same material, thus forming a one-piece disposable cap 300. The elongation of the shield 328 can be achieved mainly through the spring style bellow ring 339, which allows the use of relatively rigid material because the wall is relatively thin for the shield 328. For example, the disposable cap 300 may be formed through a two-step molding process by using just one piece of a plastic material. First, the plastic material can be used to form a shape of the optical window cover 322. Then, the spring style bellow ring 339 of the shield 328 can be formed. The thickness of the disposable cap 300 can be uniform in one embodiment.

In another embodiment, the disposable cap can have non-uniform thickness. For example, the disposable cap can have an enforced edge around the central portion which has the front concave surface and the back convex surface. The enforced corner can be in a shape of a ridge, which helps to keep the window cover in shape and prevent from bulging.

As shown in FIG. 3(D), the disposable cap 300 can comprise the locking element 327. In one embodiment, the locking element 327 can comprise one or more projections 327a. The one or more projects are radially inward and movably supported with respect to the side wall 326 of the disposable cap 300. The side wall 326 of the cap 300 can include a side wall portion of the window cover 322, a side wall portion of the shield 328 and a sidewall portion of the locking element 327. The one or more projections 327a can be configured to attach the disposable cap 300 to the eye imaging apparatus 301. For example, the one or more projections 327a can be extending radially inward to latch into the corresponding locking groove 307 on the apparatus housing 308 of the imaging apparatus 301.

The disposable cap 300 can further comprise one or more releasing tabs 327b. The one or more releasing tabs 327b can be configured to detach the disposable cap 300 from the imaging apparatus 301. In one embodiment, the one or more projections 327a and releasing tabs 327b can be disposed on a single locking element 327, on the opposite sides as shown in FIG. 3(D). The locking element 327 including the projection 327a can be made of a rigid material such as plastic, polymer, glass, metal, etc. For example, the locking element 327 including the projection 327a can be made of polycarbonate. In one embodiment, the locking element 327 including the projection 327a can be made of different material than the shield 328. The locking element 327 including the projection 327a can be connected with the shield 328 through various manufacturing process such as bonding, welding, over-molding, etc. In another embodiment, the locking element 327 including the projection 327a can be made of the same material as the shield 328 and the window cover 322, forming a one-piece disposable cap 300.

Figure 3H:
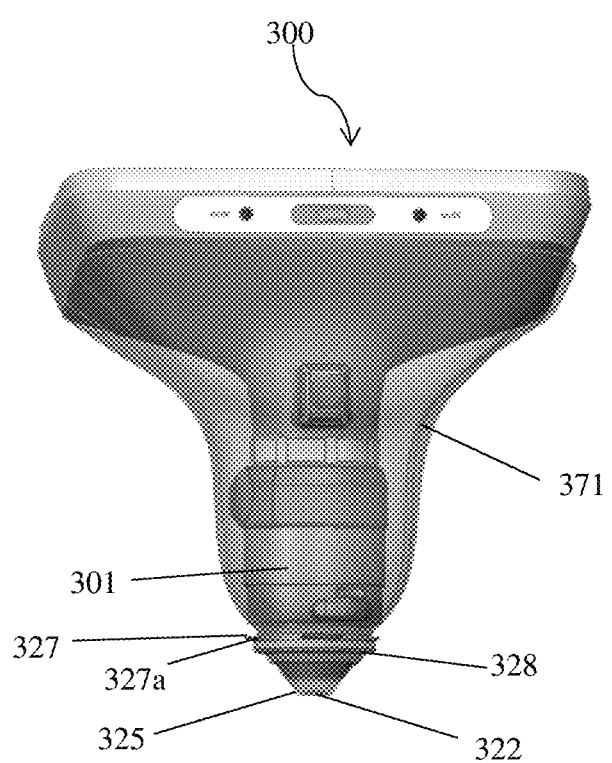
FIG. 3(H) is a perspective view of a disposable cap with a disposable sheath to cover an entire imaging apparatus.

FIG. 3(H) is a perspective view of a disposable cap 300 with a disposable sheath 371 to cover an entire imaging apparatus 301. In another embodiment, the disposable cap 300 can further comprise the disposable sheath 371 to wrap around the entire imaging apparatus 301. The disposable cap 300 with the disposable sheath 371 can cover the entire body of the imaging apparatus 301. Here the entire eye imaging apparatus 301 refers to the whole body of the apparatus, including electronic circuitry, image display, mechanic components as shown in FIG. 3(H). For example, the disposable cap 300 can have a shape matching a contour of the eye imaging apparatus 301 and enclose the entire eye imaging apparatus 301, where the locking element 327 comprising the projection 327a can be configured to be located in the middle of the disposable cap 300. In one embodiment, the sheath can be connected to the shield near the projects. The sheath 371 can comprise a resilient stretchable material. In another embodiment, the disposable cap 300 can be an integrally formed one-piece cap comprising the shield 328, the window cover 322, the distal ridge 325 and the sheath 371.

The disposable sheath 371 can be constructed with transparent plastic thin film material to form a protective barrier. The disposable cap 300 with the disposable sheath 371 is suitable to be used in sterile surgical rooms. The material for the disposable sheath 371 could be thermoplastic elastomer (TPE) or other flexible plastic or rubber. The thickness of the sheath 371 can be about 0.01 mm, 0.1 mm, 0.2 mm or any values therebetween. After the disposable sheath 371 is made and cleaned, it can be processed with standard sterilization process like radiation or ETO. The sheath 371 can be formed with a larger opening at one end, which could be sealed with an adhesive tape, and a small opening at another end. After the distal portion of the disposable cap 300 including the window cover 322 and the shield 328 is placed over the imaging apparatus 301, the sheath 371 can be slipped over the main body of the apparatus 301, and with the small opening located on the shield 328 of the disposable cap 300 near the locking projections 327a. For example, an additional elastic locking ring (not shown) can be used to secure the disposable sheath 371 over the shield 328. The disposable cap 300 with the sheath 371 can ensure that the operator of the imaging apparatus 301 never touch the surface of the imaging apparatus 301 during the operation, thus providing a total sterile environment for the imaging apparatus 301.

In yet another alternative embodiment, the disposable cap including the disposable sheath can be a one-piece disposable cap. The optical window cover, the shield and the sheath can be integrally made from the same material. The sheath can be joined with the shield of the disposable cap by bonding, gluing or over-molding techniques.

Figure 4:
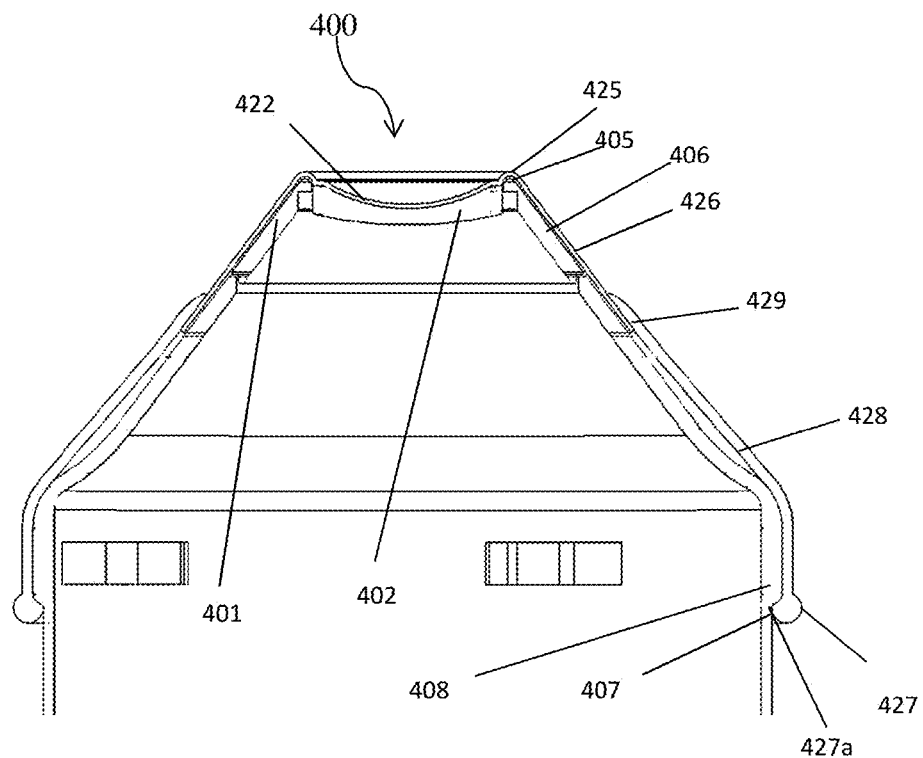
FIG. 4 is a side elevation cross-section view of a disposable cap comprising a locking ring on an eye imaging apparatus according to another embodiment of the disclosure.

FIG. 4 schematically illustrates a disposable cap 400 of the eye imaging apparatus 401 comprising a locking ring 427 in some embodiments. Unless otherwise noted, reference numerals used in FIG. 4 represent components similar to those illustrated in FIG. 3, with the reference numerals incremental by 100. In this embodiment, locking ring 427 is a thicker portion of the cap 400 at the open end of cap 400, with a projection 427a extending radially inward from the wall of the shield portion 428. The locking ring 427 can be configured to securely attach the disposable cap 400 to the eye imaging apparatus 401 during the eye examination or surgery procedure. In one embodiment, a mating locking groove 407 can be constructed into the exterior surface of the housing 408 of the eye imaging apparatus 401 such that the elastic locking ring 427 can be used to secure the disposable cap 400 onto the housing 408. In another embodiment, the locking groove 407 can be disposed into the exterior surface of the window housing 406 and a mating locking ring feature can be disposed on an interior surface of the disposable cap 400. In some embodiments, one or both the locking features extend around the entire circumferences of the eye imaging apparatus 401 and disposable cap 400. In some embodiments, one or both the locking features extend along only a portion or portions of the circumferences of the eye imaging apparatus 401 and disposable cap 400, as in subsequently described embodiments. As in earlier embodiments, the disposable cap 400 has an optical window cover 422 covering an optical window 402 of the eye imaging apparatus 401. The disposable cap 400 can also have a ridge 425 extending distally and radially outward from the window cover 422 and a side wall 426 extending proximally and radially outwardly from the ridge 425 toward the open end of the disposable cap 400. The optical window cover 422, the ridge 425 and the side wall 426 may have the same dimensions, shape and properties as the optical window cover 322, the ridge 325 and the side wall 326 discussed above with respect to FIGS. 3(A)-(G). When disposable cap 400 is placed over eye imaging apparatus 401, cap ridge 425 engages ridge 405 of the eye imaging apparatus 401 to prevent deformation of optical window cover 422 during the cap placement process.

In various embodiments, the disposable cap 400 can further comprise a second portion which can be a shield 428. The shield 428 can be configured to cover at least a portion of the imaging apparatus housing 408 or the window housing 406. The shield 428 can be configured to help securely attaching the disposable cap 400 to the imaging apparatus 401. The shield 428 can also be configured to provide more thorough protection against cross-contamination among patients. Both the length of the shield 428 and the shape of shield 428 can vary, not limited to the exemplary illustrations shown in FIG. 4. Accordingly, the disposable cap 400 can have various shapes, not limited to the exemplary illustrations shown in FIG. 4 as well. In one embodiment, the shield 428 can be configured to cover a portion of the apparatus housing 408 as shown in FIG. 4. In other embodiment, the shield 428 can be configured to cover the window housing 406. In yet another embodiment, the shield can be configured to cover the window housing 406 and a portion of the apparatus housing 408. In another alternative embodiment, the shield 428 can be an elongated tube or sheath that covers most of the eye imaging apparatus 401.

In yet another embodiment, the disposable cap 400 including the optical window cover 422 and the shield 428 can be configured to cover the entire eye imaging apparatus 401. Here the entire eye imaging apparatus refers to the whole body of the apparatus, including electronic circuitry, image display, mechanical components which are not shown in FIG. 4. For example, the disposable cap 400 can have a shape matching a contour of the eye imaging apparatus 401 and enclose the entire eye imaging apparatus 401, where the locking element 427 can be configured to be located in the middle of the disposable cap 400. In an alternative embodiment, the shield 428 can be simply a plane perpendicular to the optical axis of the imaging apparatus 401. Yet in another embodiment, the disposable cap 400 can only comprise the optical window cover 422 without the shield 428, where the locking element 427 can be disposed on the optical window cover 422. The disposable cap 400 may attach to eye imaging apparatus 401 by stretching or otherwise radially expanding the locking ring 427 and shield 428, sliding the cap 400 over the instrument, then permitting the projection 427a of locking ring 427 to move radially inward to enter the groove 407 and the shield 428 to radially contract to grip the apparatus housing 408 of the eye imaging apparatus 401.

As shown in FIG. 4, the shield 428 of the disposable cap 400 can comprise elastic or flexible materials such as rubber, or rubber like materials according to one embodiment. For example, the shield 428 can comprise thin wall structure of latex, Vinyl, Nitrile and other elastic materials. The elastic properties permit the shield 428 to stretch as the locking ring 427 is pulled proximally after the window cover 422 engages the optical window 402 of the eye imaging apparatus 401. The shield 428 can have a small overlapping area 429 over the optical window cover 422. The clear optical window cover 422 and the shield 428 can be connected together at the joint section of the overlapping area 429. The clear optical window cover 422 and the shield 428 can be joined by various processes such as bonding, gluing, overmolding or other manufacturing processes. The elastic locking ring 427 can be disposed at an open proximal end of the disposable cap 400. The disposable cap 400 can be stretched to have the elastic ring 427 secured in the locking groove 407. The clear optical window cover 422 can be placed over the optical window 402 securely.

Figure 5:
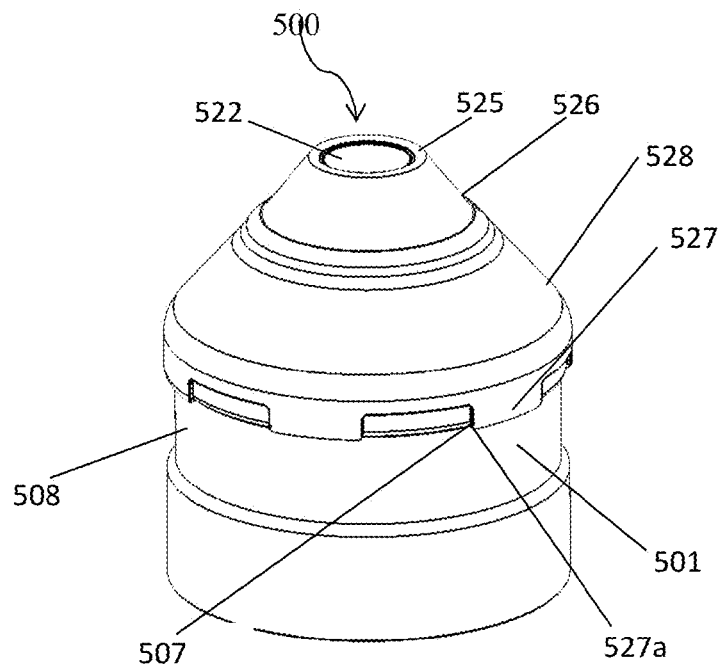
FIG. 5 is a perspective view of a disposable cap further comprising a shield according to another embodiment.

FIG. 5 schematically illustrates a disposable cap 500 with a shield 528 comprising rigid or semi-rigid plastic materials according to another embodiment of the disclosure. Unless otherwise noted, reference numerals used in FIG. 5 represent components similar to those illustrated in FIG. 3, with the reference numerals incremental by 200. The shield 528 of the disposable cap 500 can comprise rigid or semi-rigid plastic materials, which can be suitable for mass production. The shield 528 may comprise at least one locking element 527 with a projection 527a extending inwardly. The eye imaging apparatus 501 may comprise at least one mating groove 507 disposed on the apparatus housing 508 configured to match with the projection or projections 527a of the disposable cap 500. The locking projection or projections 527a can be constructed to be rigid enough to be clicked into the at least one mating locking groove 507 in order to secure the disposable cap 500, but with enough flexibility to be pulled out by force when the examination or operation is finished with or without the use of additional tools. The disposable cap 500 may comprise one continuous locking projection 527a, or a plurality of locking projections 527a. The number of the locking projections 527a can be three in one embodiment. The number of the locking projections 527a can be four in another embodiment. The number of the locking projections 527a can be at least one, and in some embodiments as many as possible that can be manufactured. For example, the number of the locking projections 527a can be 6 as shown in FIG. 5. In some embodiments, for example, the locking projection 527a can have a length perpendicular to the radial direction between 3 mm and 28 mm, a width inwardly along the radial direction between 0.5 mm and 3 mm, a thickness along the direction of the optical axis of the imaging apparatus 501 between 1 mm and 10 mm. The mating groove 507 of the apparatus 501 can be slighter larger than the locking projections 527a. The mating groove 507 can have a length perpendicular to the radial direction between 60 mm and 250 mm, a width inwardly along the radial direction between 0.5 mm and 5 mm. As the disposable cap 500 is advanced onto eye imaging apparatus 501, the projections 527a move radially outward until they meet groove 507, at which point they move radially inward to grip the housing 508 of imaging apparatus 501. Once in place, the optical window cover 522 of disposable cap 500 lines up with the optical window of the eye imaging apparatus 501. As in earlier embodiments, the disposable cap 500 can have an optical window cover 522 covering an optical window of the eye imaging apparatus 501. The disposable cap 500 can also have a ridge 525 extending distally and radially outward from the window cover 522 and a side wall 526 extending proximally and radially outwardly from the ridge 525 toward the open end of the disposable cap 500. The optical window cover 522, the ridge 525 and the side wall 526 may have the same dimensions, shape and properties as the optical window cover 322, the ridge 325 and the side wall 326 discussed above with respect to FIGS. 3(A)-(G). In particular, as in the other embodiments, when cap 500 is pulled over eye imaging apparatus 501, an inside surface of cap ridge 525 engages a corresponding ridge (not shown) on the eye imaging apparatus to minimize deformation of the optical window cover 522 during the cap mounting process.

Figure 6:
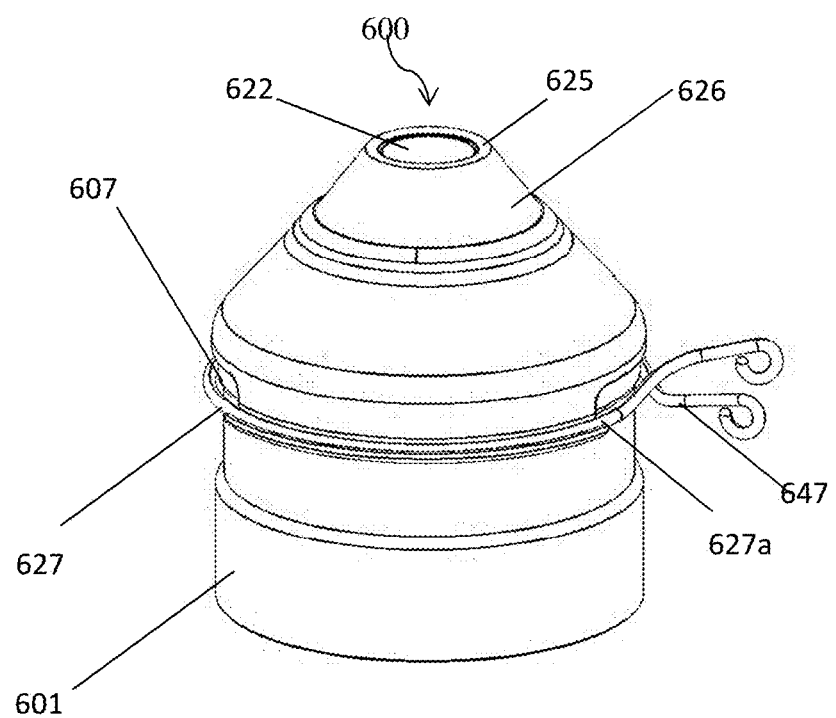
FIG. 6 is a perspective view of a disposable cap comprising at least one extended tab.

FIG. 6 schematically illustrates a disposable cap 600 comprising at least one extended tab 647. Unless otherwise noted, reference numerals used in FIG. 6 represent components similar to those illustrated in FIG. 3, with the reference numerals incremental by 300. In one embodiment, a rigid open ring 627 having one or more tab or tabs 647, which could be made of metal or plastic, can be disposed at the open end of the disposable cap 600. Ring 627 acts as one turn of a torsion spring to apply a force to the open end of cap 600 to form a radially inward projection 627a. The one or more tab or tabs 647 can extend from an open portion of rigid ring 627. When advancing cap 600 onto eye imaging apparatus 601, tabs 647 move apart as the ring 627 radially expands, then move back toward each other under the spring action of ring 627 when ring 627 reaches groove 607 on the eye imaging apparatus 601 to secure the disposable cap 600 into the locking groove 607 so that optical window cover 622 lines up with the optical window of eye imaging apparatus 601. The tabs 647 also enable the user to release the disposable cap 600 from the imaging apparatus 601 after the examination is finished by providing leverage to expand ring 627 out of groove 607. The disposable cap 600 can have an optical window cover 622 covering an optical window of the eye imaging apparatus 601. The disposable cap 600 can also have a ridge 625 extending distally and radially outward from the window cover 622 and a side wall 626 extending proximally and radially outwardly from the ridge 625 toward the open end of the disposable cap 600. The optical window cover 622, the ridge 625 and the side wall 626 may have the same dimensions, shape and properties as the optical window cover 322, the ridge 325 and the side wall 326 discussed above with respect to FIGS. 3(A)-(G). As in the other embodiments, when cap 600 is pulled over eye imaging apparatus 601, an inside surface of cap ridge 625 engages a corresponding ridge (not shown) on the eye imaging apparatus to minimize deformation of the optical window cover 622 during the cap mounting process.

Figure 7:
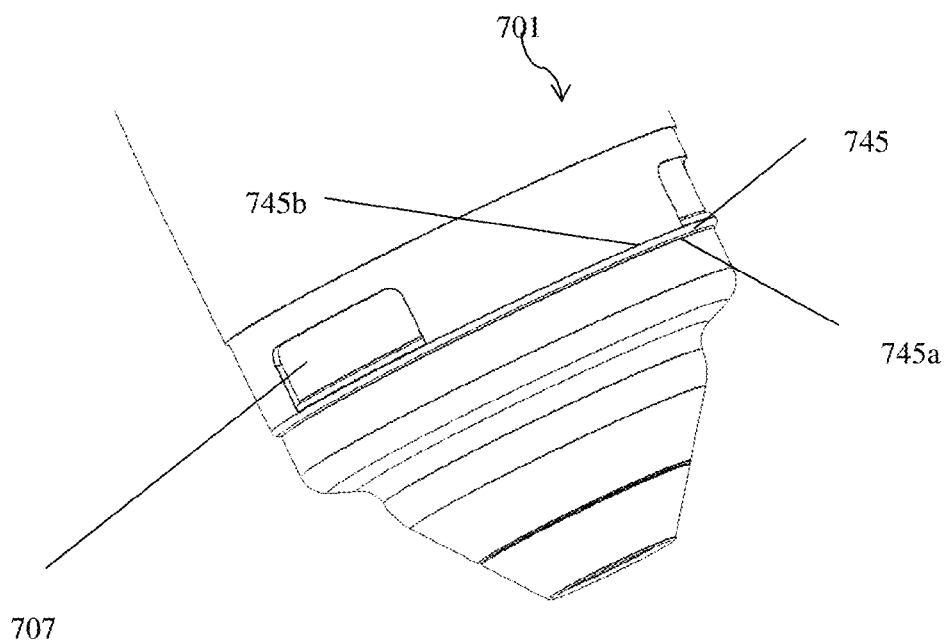
FIG. 7(A) is a side view of an eye imaging apparatus comprising at least one locking ridge in order to form a locking groove on the apparatus housing.
FIG. 7(B) is a cross-sectional view of a portion of the eye imaging apparatus of FIG. 7(A).
Figure 7B:
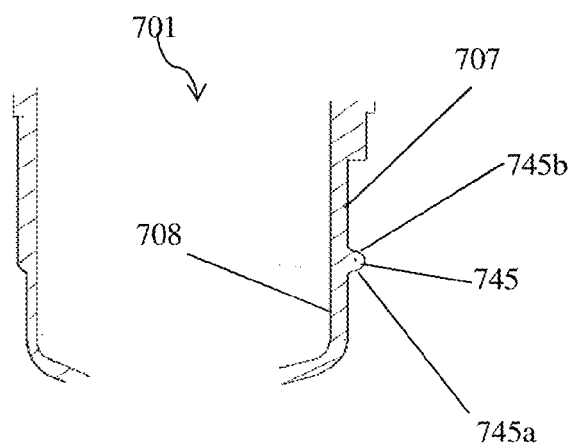

FIG. 7(A) and FIG. 7(B) schematically illustrate an eye imaging apparatus 701 comprising at least one locking ridge 745 extending radially outward in order to define the locking groove 707 on the apparatus housing 708. In some embodiments, the apparatus housing 708 may be too thin to have a locking groove 707 disposed therein. The locking ridge 745 may be disposed on the apparatus housing 708 to form the locking groove 707 with the rest of the housing 708. The locking ridge 745 may comprise a front slope 745a and a back slope 745b. The front slope 745a of the locking ridge 745 can be configured to attach the disposable cap to the imaging apparatus 701 easily, or to make the imaging apparatus 701 easily inserted into the disposable cap. The back slope 745b can be configured to lock the disposable cap to the imaging apparatus 701, and also allow the imaging apparatus 701 being pulled out from the disposable cap. The height of the locking ridge 745 can be between 0.5 mm and 3 mm. The width of the locking ridge 745 can be between 0.5 mm and 4 mm. In some embodiments, there can be multiple locking ridge sections forming the locking ridge 745, each extending part way around the circumference of the housing 708. The number of the locking ridge sections forming the locking ridge 745 can be three in one embodiment. The number of locking ridge sections forming the locking ridge 745 can be four in another embodiment. In the embodiment shown in FIG. 7(A), the locking ridge 745 forms a continuous ring. The front slope 745a of the locking ridge 745 can be between 0.25 mm and 3 mm. The back slope 745b of the locking ridge 745 can be between 0.25 mm and 2 mm. In some embodiments, one or more locking grooves 707 on the housing 708 correspond to one or more radially inward projections in a disposable cap, for example as shown in FIG. 7(A) with 3 locking grooves, and can have a length perpendicular to the radial direction between 6 mm and 40 mm, a width inwardly along the radial direction between 0.5 mm and 3 mm, a depth along the direction of the optical axis of the imaging apparatus 701 between 1 mm and 10 mm. The number of locking grooves 705 can be three in one embodiment. The number of locking grooves 705 can be four in another embodiment. The number of locking grooves 705 on the housing can be at least one, and as many as possible to be manufactured, including a continuous locking groove that encircles the entire imaging apparatus 701 which effectively eliminates the side-wall structure of locking groove.

FIG. 8(A) to FIG. 8(E) schematically illustrate a disposable cap 800 comprising at least one locking element 827 comprising a radially inward projection 827a and at least one releasing tab 827b according to one embodiment. The releasing tab or tabs 835 can be, configured to detach or unlock the disposable cap 800 from the eye imaging apparatus 801. Unless otherwise noted, reference numerals used in FIG. 8 represent components similar to those illustrated in FIG. 3, with the reference numerals incremental by 500. The eye imaging apparatus 801 can comprise an optical window 802, a window housing 806, and an apparatus housing 808. The apparatus housing may comprise at least one locking ridge 845 which defines at least one locking groove 807. The disposable cap 800 can comprise an optical window cover 822 and a shield 828. In some embodiments, the shield 828 of the disposable cap 800 can comprise plastic materials, which are suitable for mass production. The projections 827a of the locking elements 827 and the releasing tab or tabs 827b can be disposed on the shield 828 as single piece construction or as a separated component bonded to the shield 828.

The disposable cap 800 may comprise one continuous projection 827a, or a plurality of locking element projections 827a. The number of the locking projections 827a can be three in one embodiment. The number of the locking projections 827a can be four in another embodiment. The number of the locking projections 827a can be at least one, and can be as many as possible that can be manufactured. Same numbers of locking grooves 807 can be built into the exterior surface of the apparatus housing 808 to be fit with the matching locking projections 827a on the disposable cap 800. The width of the locking groove 807 can be slightly larger than the width of the locking projections 827a. As a result, rotation of the disposable cap 800 relative to the apparatus housing 808 is prevented when the locking projection or projections 827a are locked into the locking groove or grooves 807. In an alternative embodiment, only one single continuous locking groove is constructed on the apparatus housing while a plurality of locking projections 827a are used. The friction between the locking projections and surface of the locking groove can be sufficient to prevent the rotation of the disposable cap 800 relative to the apparatus housing 808.

Figure 8A:
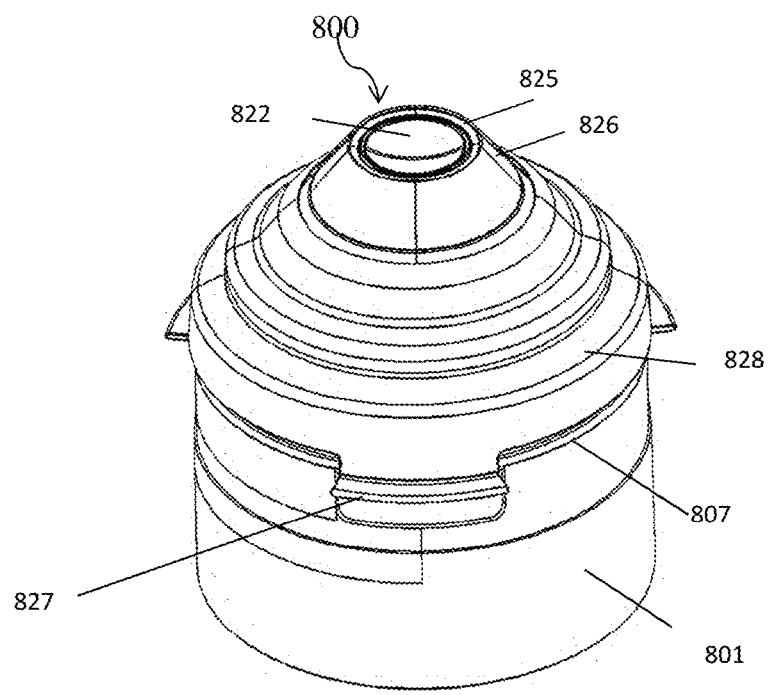
FIG. 8(A) is a perspective view of a disposable cap comprising at least one locking projection and at least one releasing tab according to one embodiment of the disclosure.
Figure 8B:
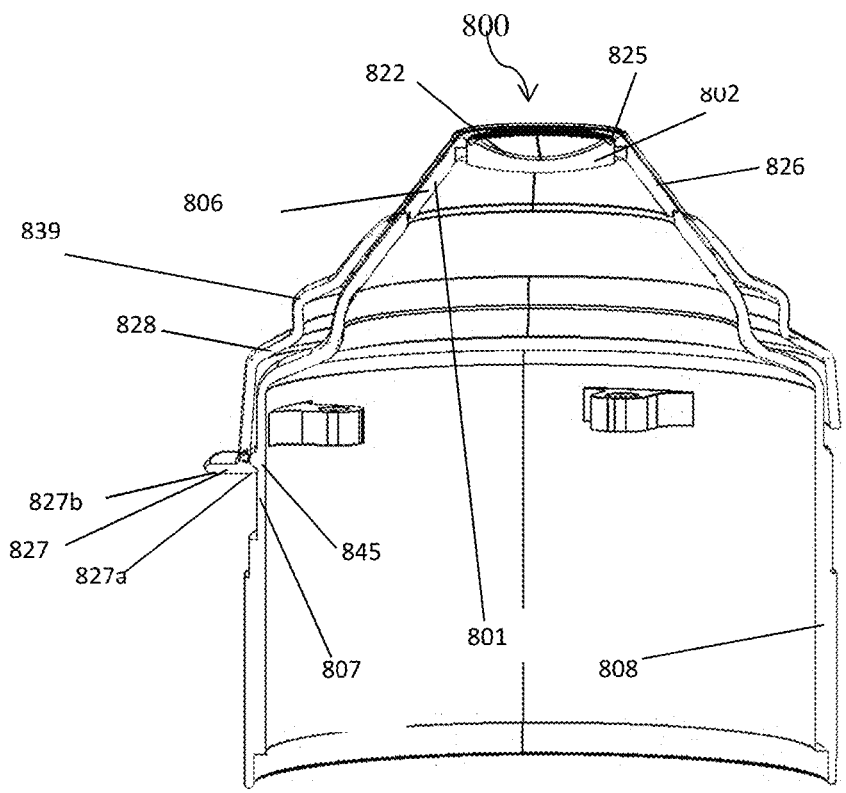
FIG. 8(B) is a cross-sectional view of the disposable cap of FIG. 8(A).

As shown in FIG. 8(B), the disposable cap 800 can further comprise at least one releasing tab 827b. The releasing tab or tabs 827b can be positioned at the same location as the locking projection or projections 827a at the open end of the disposable cap 800, where the locking projection or projections 827a extend inwardly towards the optical axis of the imaging apparatus 801, and the releasing tab or tabs 827b extend outwardly away from the optical axis. The disposable cap 800 may comprise one continuous releasing tab 827b, or a plurality of releasing tabs 827b. The number of the releasing tabs 827b can be three in one embodiment. The number of the releasing tabs 827b can be four in another embodiment. The number of the releasing tabs 827b can be at least one, and can be as many as possible that can be manufactured. For example, in some embodiments as shown in FIG. 8 with 3 locking projections 827a, the releasing tab 827b can have a length perpendicular to the radial direction between 6 mm and 60 mm, a width inwardly along the radial direction between 1 mm and 10 mm, and a thickness along the direction of the optical axis of the imaging apparatus 801 between 0.5 mm and 4 mm.

In various embodiments, the disposable cap 800 may further comprises a spring style bellow ring 839 disposed on the shield 828. For example, the spring style structure or bellow ring 839 may comprise at least one corner in one embodiment. The corner can be about 30 degrees, 60 degrees, 90 degrees, 120 degrees, 150 degrees or any values therebetween. During the attaching process, the disposable cap 800 may be extended to a larger length along the optical axis direction of the imaging apparatus 801 than the length of the disposable cap 800 in the locking position to allow the open proximal end of the disposable cap 800 to pass the locking ridge or ridges 845. The spring style structure or bellow ring 839 can be configured to allow the disposable cap 800 to elongate after the inside surface of ridge 825 engages the corresponding ridge of the eye imaging apparatus 801 and for locking elements 827 to move radially outward against the spring action of ring 839 as they pass over the locking ridge 845. Once the locking projection or projections 827*a* are locked into the locking groove or grooves 807 of the apparatus housing 808, the disposable cap 800 can return to the normal length with nominal elongation of the shield 828. The spring style of structure or bellow ring 839 is configured to allow the flexibility of the disposable cap 800 along the optical axis direction during the attaching process and extra elongation of the shield 828 when the one or more projections 827*a* are in the locking position.

Figure 8C:
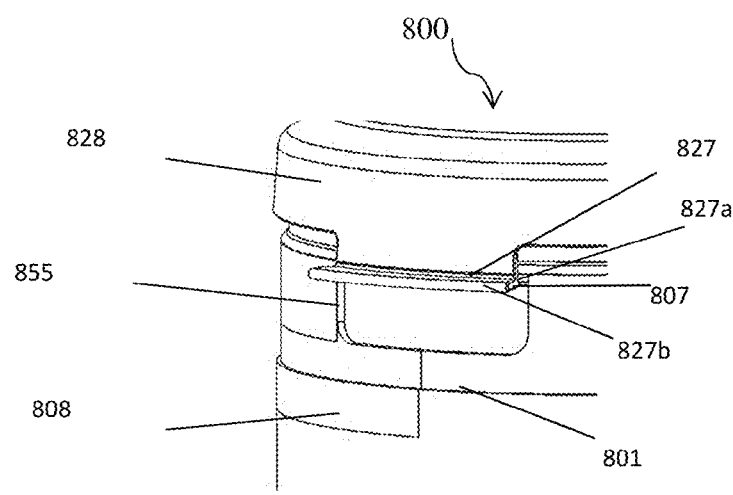
FIG. 8(C) is a perspective view of a portion of the disposable cap of FIG. 8(A) that illustrates a sidewall of a locking groove of the imaging apparatus configured to stop the rotation of the disposable cap, thus locking the disposable cap to the imaging apparatus.

Before a medical procedure such as an eye examination or surgery, the disposable cap 800 may be placed over an imaging apparatus 801 and pushed onto the imaging apparatus 801 with slight force. This action pulls the distal end of cap back against the action of spring 839 and pushes projections 827*a* radially outward as the disposable cap 800 moves over the housing 808 of the eye imaging apparatus 801. As in the other embodiments, the ridge 825 minimizes deformation of the optical window cover 822 during the cap mounting process. Then the disposable cap 800 can be rotated until the locking projections 827*a* move radially inward and click into the mating locking grooves 807. In one embodiment, the locking groove 807 comprises a sidewall 855, which is configured to stop the rotation of the disposable cap 800, thus locking the disposable cap 800, as shown in FIG. 8(C). The locking projection or locking projections 827*a* can be constructed to be rigid enough to be clicked into the locking groove or locking grooves 807 on the apparatus housing 808 in order to secure the disposable cap 800 during the medical procedure. When in place, the optical window cover 822 of the disposable cap 800 lines up with the optical window 802 of eye imaging apparatus 801. The disposable cap 800 can have an optical window cover 822 covering an optical window of the eye imaging apparatus 801. The disposable cap 800 can also have a ridge 825 extending distally and radially outward from the window cover 822 and a side wall 826 extending proximally and radially outwardly from the ridge 825 toward the open end of the disposable cap 800. The optical window cover 822, the ridge 825 and the side wall 826 may have the same dimensions, shape and properties as the optical window cover 322, the ridge 325 and the side wall 326 discussed above with respect to FIGS. 3(A)-(G).

Figure 8D:
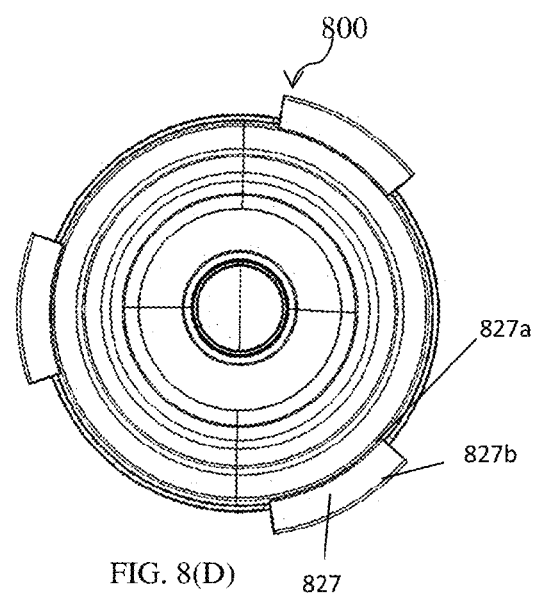
FIG. 8(D) is a top view of the disposable cap of FIG. 8(A) showing the releasing tabs and the locking projections.

FIG. 8(D) is a top view of the releasing tabs 827*b* and the locking projections 827*a* according to one embodiment. The width of the releasing tabs 827*b* can be larger than the locking projections 827*a*. For example, the width of the releasing tabs 827*b* can be 20%, 50%, 100%, 200%, or 500%, 1000% larger or any values therebetween than the width of the locking projections 827*a*. The locking projections 827*a* can extend inwardly into the locking groove 807 underneath the locking bridge 845, thus locking the disposable cap 800 to the imaging apparatus 801.

Figure 8E:
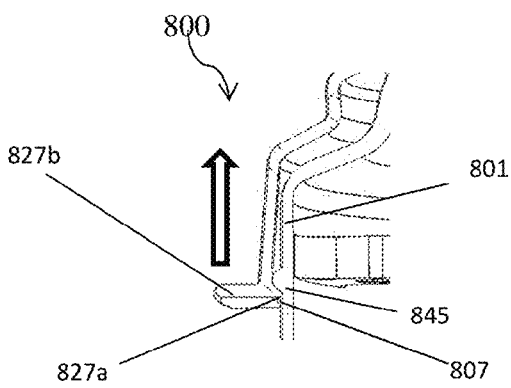
FIG. 8(E) is a partial cross-sectional view of the disposable cap of FIG. 8(A) showing how the locking projections can be moved out of the locking grooves by pulling the releasing tabs toward the frontal direction of the imaging apparatus.

Referring to FIG. 8(E), the locking projection or projections 827*a* can be moved out of the locking groove or grooves 807 by pulling the releasing tab or tabs 827*b* toward the distal direction of the imaging apparatus 801 after the procedure. The user could pull out the disposable cap 800 by simply pulling the releasing tabs 827*b* with fingers. Although 3 pairs of locking projections/grooves are shown in the figures, a larger number of locking projections/grooves pairs or a single locking projection/groove pair can also be used. The larger width of the releasing tabs 827*b* can help to pull the locking projection or projections 827*a* out of the locking groove or grooves 807. The back slope 845*b* of locking bridge 845 can also help to easily detach the disposable cap 800 from the imaging apparatus 801. A portion or portions of disposable cap 800 adjacent to releasing tab(s) 827*b*, such as spring structure or bellow ring 839, may be configured to be reasonably flexible. With this arrangement, when release tab(s) 827*b* are urged towards the distal end of imaging apparatus 801, the flexible portion(s) cause projections 827*a* to pivot outwardly away from locking groove(s) 807, further facilitating the release of disposable cap 800.

The disposable cap can comprise a variety of locking elements, not limited to the illustrated locking elements discussed above. The locking element is a broad term including physical structure and texture structure, or any mechanism that are capable of securely attaching the disposable cap to the imaging apparatus. For example, the disposable cap can comprise a locking groove or a plurality of locking grooves which matches a locking projection or a plurality of locking projections on the housing of the imaging apparatus in another embodiment. The disposable cap can comprise an inner surface with certain friction to prevent the disposable cap from falling off the eye imaging apparatus in another embodiment. The disposable cap may comprise an outer surface that can be clamped with the housing of the imaging apparatus to secure the disposable cap in yet another embodiment.

Figure 9:
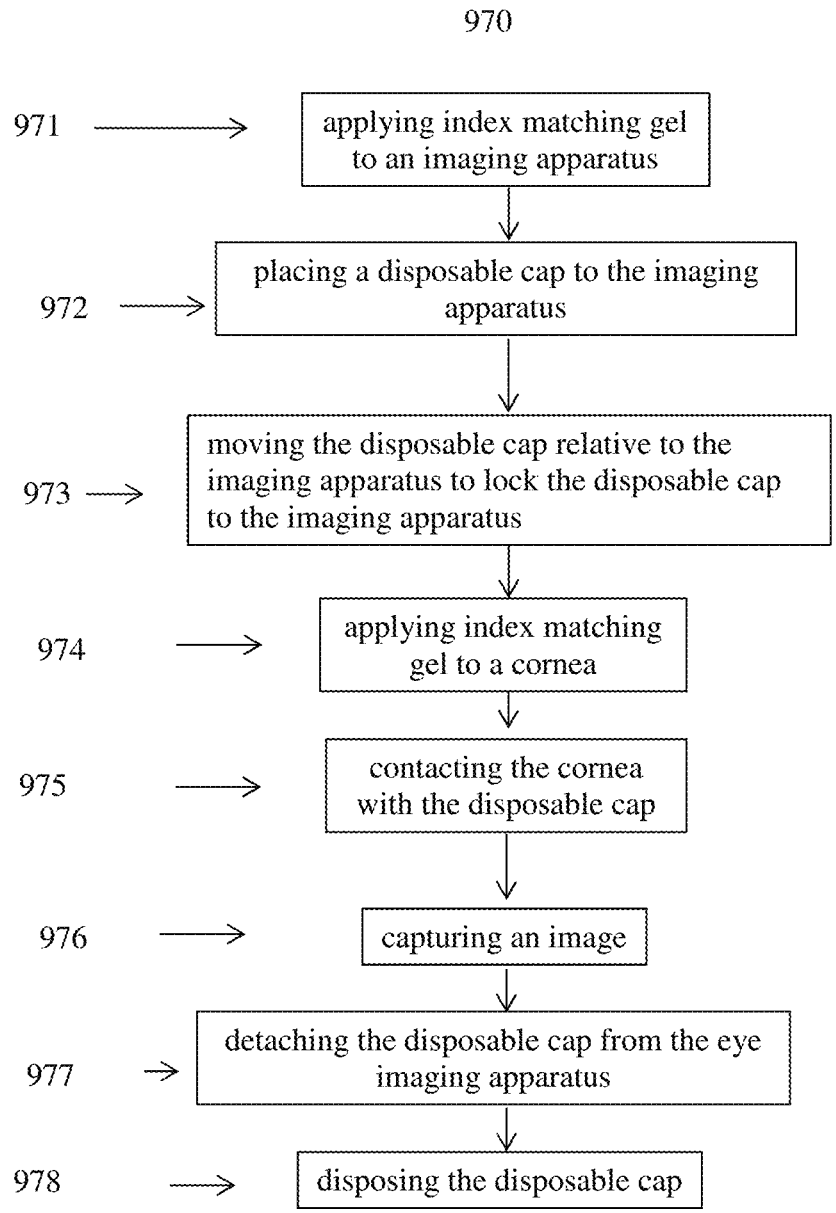
FIG. 9 is a flow chart of a method of preventing cross-contamination caused by an eye imaging apparatus with an optical window configured to contact a cornea of an eye of a patient according to one embodiment of the disclosure.

FIG. 9 schematically illustrates a method 970 of preventing cross-contamination caused by an eye imaging apparatus with an optical window configured to contact a cornea of an eye of a patient according to one embodiment of the disclosure. The method comprises the following steps. First, applying an index matching gel or water to a front surface of the optical window of the eye imaging apparatus as shown in block 971, where the eye imaging apparatus comprises at least one locking groove. The method comprises placing a disposable cap to the eye imaging apparatus as in block 972, where the disposable cap comprises an optical window cover configured to match a contour of the front surface of the optical window and a locking element. The method further comprises moving the disposable cap relative to the imaging apparatus either by pulling the disposable cap along an optical axis of the optical window toward the optical window, or by rotating the disposable cap clockwise or counter clock-wise around the optical axis of the optical window. Then the disposable cap can be locked to the eye imaging apparatus when the locking element and the at least one locking groove click, as shown in block 973. The method further comprises disposing index matching gel to the cornea of the eye as in block 974. In some embodiments, the index matching gel may be disposed to the concave surface of the disposable cap as well. The method further comprises contacting the cornea with the disposable cap where the disposable cap is locked with the eye imaging apparatus as in block 975, then capturing an image of the eye using the imaging apparatus as in block 976.

The method further comprises detaching the disposable cap from the eye imaging apparatus by removing the locking element from the locking groove as shown in block 977, and disposing the disposable cap as shown in block 978. In some embodiments, the eye imaging apparatus further comprises one or more releasing taps. The method comprises pulling the releasing tabs towards the frontal direction of the imaging apparatus to release the locking clicks from the locking grooves, thus detaching the disposable cap from the imaging apparatus after the medical procedure. The method further comprises disposing the disposable cap after the medical procedure.

FIGS. 10(A) to 10(D) schematically illustrate a sterile disposable packaging shell 1060 of a disposable cap according to one embodiment of the disclosure. The sterile packaging shell 1060 can be constructed as a completely sealed packaging. The disposable packaging shell 1060 can comprise a sealing lid 1061 at a top end to keep the shell completely sealed from the environment. The disposable cap can be placed inside the packaging shell 1060 after being manufactured and cleaned or sterilized. The sterilization process, like radiation and ETO, can also be implemented after the disposable cap is sealed in the packaging shell 1060. The seal lid can be made from materials not permeable to water and gas, or special materials which are permeable to gas and water vapor while acting as a barrier membrane to dust or biohazards. The shell 1060 can protect the disposable cap and keep the disposable cap (not shown) sterile before it is applied to the imaging apparatus. Before the medical procedure, the sealing lid 1061 of the individual sealed packaging shell can be opened and peeled off. The sterile disposable cap can be exposed for use.

The shell 1060 can comprise a head 1069 at a bottom end. The head can comprise an indentation 1062 at a central portion to protect the concave front surface of the optical window cover of the disposable cap in one embodiment. The shell 1060 can be configured to not only protect the disposable cap from damage and contamination during the transportation, but also act as a locking/unlocking element during the attaching and detaching process. After the medical procedure, the shell 1060 can be a storage unit for the used disposable cap.

Figures 10A, 10B:
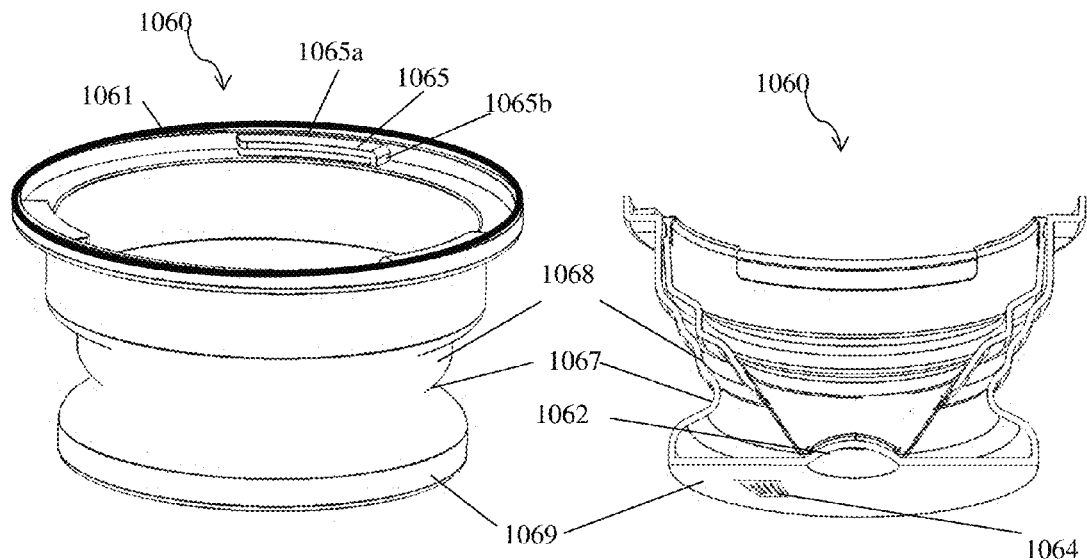
FIG. 10(A) is a perspective view of a sterile disposable packaging shell of a disposable cap according to one embodiment of the disclosure.
FIG. 10(B) is a cross-sectional view of the sterile disposable packaging shell of FIG. 10(A).

FIG. 10(A) schematically illustrates a perspective view of the packaging shell 1060. The packaging shell 1060 can be constructed with plastic material with relatively large thickness in order to maintain the stiffness of the shell 1060. The packaging shell 1060 can be made by injection molding or formed from a one piece preform. Such construction ensures the reliable sealing and protection for the sterile disposable cap during the radiation sterilization process if required.

FIG. 10(B) schematically illustrates a section view of the packaging shell 1060. The shell 1060 can comprise a main portion 1068 configured to support the shield of the disposable cap. The indentation 1062 can comprise a convex inside surface configured to match a shape of the concave front surface of the window cover of the disposable cap. The indentation 1062 can help support the clear optical window cover when the imaging apparatus is plugged in from the opposite end of the shell 1060. The shell 1060 can further comprise a head 1069 and a narrow waist 1067 between the main portion 1068 and the head 1069. The head 1069 can be configured to support the shell 1060 with the disposable cap inside during the attaching and detaching process. In some embodiments, the inside surface of the head 1069 can further comprise a groove portion extending radially outward from the convex surface to match a ridge of the disposable cap.

The narrow waist 1067 is configured to be held by the user to keep the shell 1060 in place to facilitate the attaching and detaching process. The head 1069 can have a larger diameter than the waist 1067 as shown. The shell 1060 can have an overall height between 15 mm and 60 mm. The overall height of the shell 1060 can be outside the above range as well. The shell 1060 can have a diameter at an open end between 20 mm and 60 mm. The shell 1060 can have a diameter at the waist 1067 between 10 mm and 40 mm. The shell 1060 can have a diameter of the head 1069 between 20 mm and 60 mm. The diameters of the shell 1060 can be outside the above ranges as well. The shell 1060 can have a thickness between 0.5 mm and 4 mm. The thickness of the shell 1060 can be outside the above range as well.

The disposable packaging shell 1060 can further comprise an identifying element 1063 with unique identification information (ID). The identifying element 1063 on the disposable packaging shell 1060 can be configured to uniquely identify the disposable cap. For example, a barcode, two dimensional identification pattern, or radio frequency identification chip can be printed to, or embedded into the body of the packaging shell 1060, to uniquely identify each individual disposable cap. The identifying element 1063 can also be placed onto other surfaces of the packaging shell 1060, or even the sealing lid.

Figures 10C, 10D:
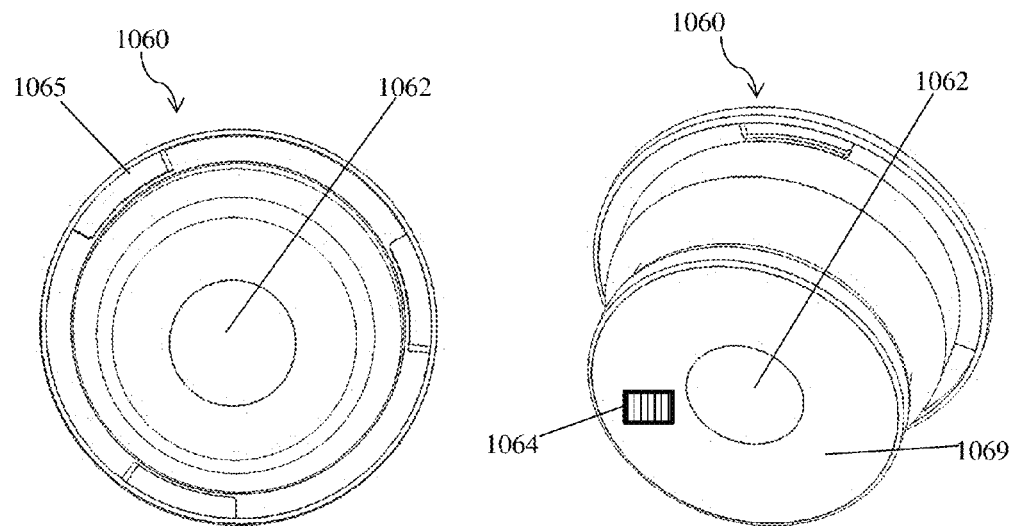
FIG. 10(C) is a top view of the sterile disposable packaging shell of FIG. 10(A).
FIG. 10(D) is another perspective view of the sterile disposable packaging shell of FIG. 10(A).

FIG. 10(C) schematically illustrates a top view of the packing shell 1060. The sterile disposable packaging shell 1060 can comprise one or more radially inward shell tabs 1065 that matches the mating radially outward releasing tabs 835 of the disposable cap 800 as shown in FIG. 8(A). Referring to FIG. 10(A) and FIG. 10(C), each of the one or more shell tabs can have an L-shape comprising a long portion 1065a and a short stopper 1065b. The long portion 1065a can be perpendicular to the optical axis of the imaging apparatus, or parallel to the head 1069. The short stopper 1065b can be can be parallel to the optical axis of the imaging apparatus, or perpendicular to the head 1069.

A perspective view of the packaging shell 1060 looking from the front direction is schematically illustrated in FIG. 10(D). The inside convex surface of the indentation 1062 for supporting the optical window cover of the disposable cap can be disposed at the center of the head 1069. In one embodiment, the identification bar code 1064 can be printed on the head 1069.

The packaging shell 1060 can protect the disposable cap from contamination from environment and provide physical protection during transportation for the disposable cap to prevent it being crashed accidentally. The packaging shell 1060 can further allow the operator to attach and detach the disposable cap from the imaging apparatus without contacting the disposable cap directly. Furthermore, the packaging shell 1060 can provide safe storage for the used cap which could be contaminated during the examination. In some embodiments, the packaging shell 1060 can comprise an indentation 1062 at the head 1069 at the bottom of the packaging shell 1060 to protect the concave surface of the disposable cap.

The packaging shell can have a variety of embodiments, not limited to the exemplary embodiment illustrated in FIG. 10(A) to FIG. 10(D). For example, the short stopper can be positioned on a side wall of the packaging shell separated from the shell tabs. The packaging shell can also comprise another locking element to lock the packaging shell to the disposable cap. For example, the packaging shell can comprise one or more removable clamps, which can be configured to be removed to enable the disposable cap to be attached to the eye imaging apparatus, and be repositioned to enable the disposable cap to be detached from the eye imaging apparatus.

Figure 11A:
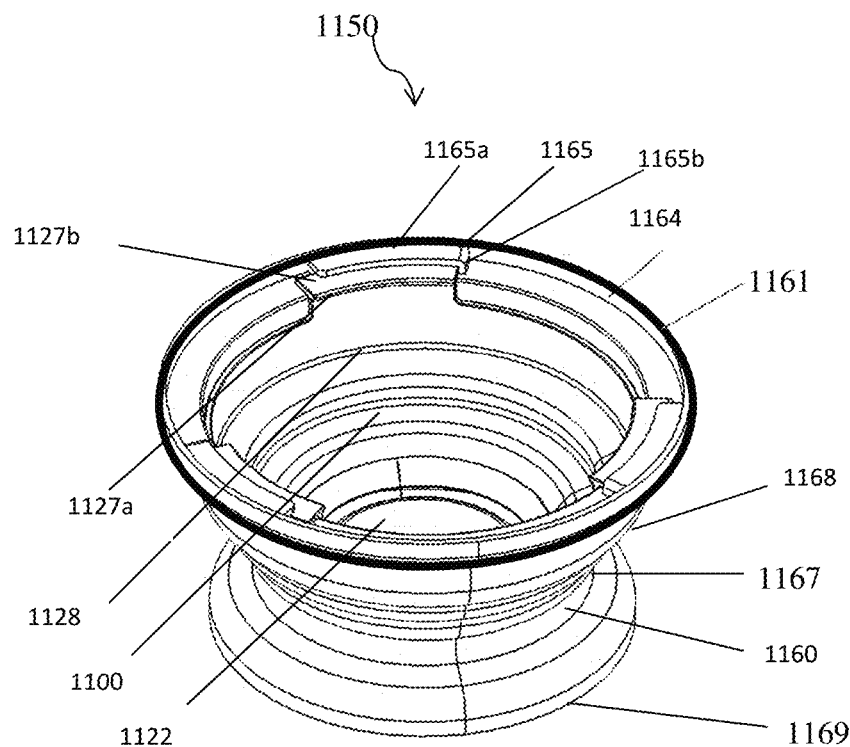
FIG. 11(A) is a perspective view of a plug-in disposable system comprising a disposable cap and a disposable packaging shell according to one embodiment of the disclosure
Figure 11B:
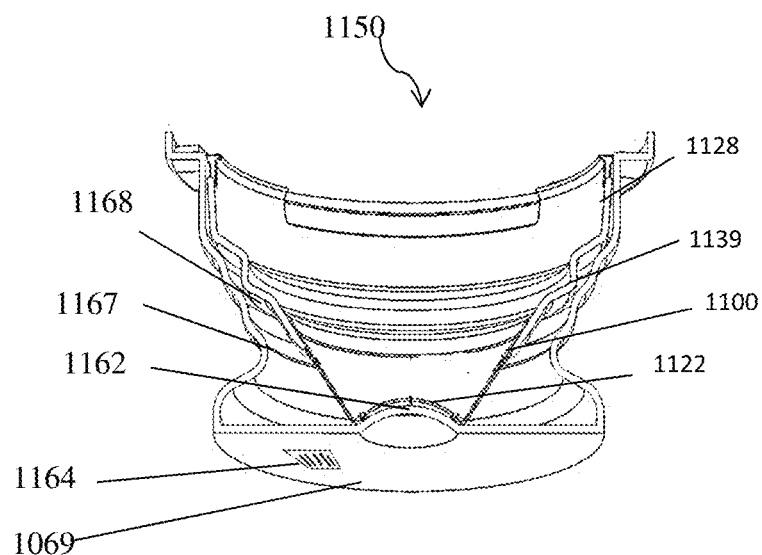
FIG. 11(B) is a cross-sectional view of the plug-in disposable system of FIG. 11(A).
Figure 11C:
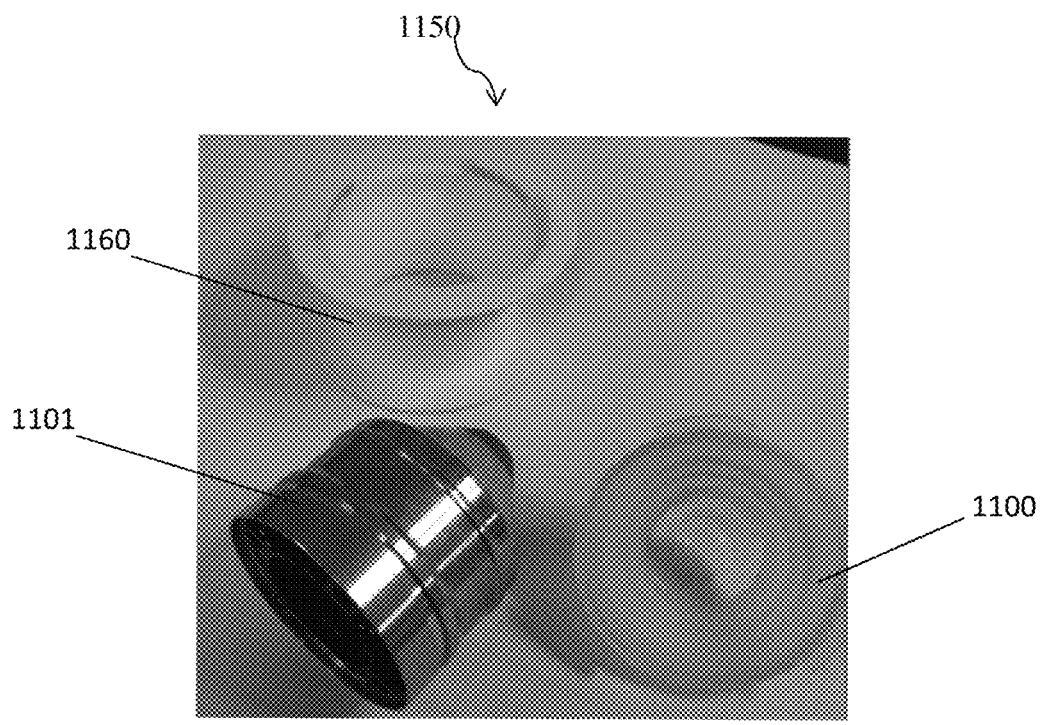
FIG. 11(C) is a photo of the eye imaging apparatus, the disposable cap and the disposable packaging shell according to the embodiment of FIG. 11(A).
Figure 11D:
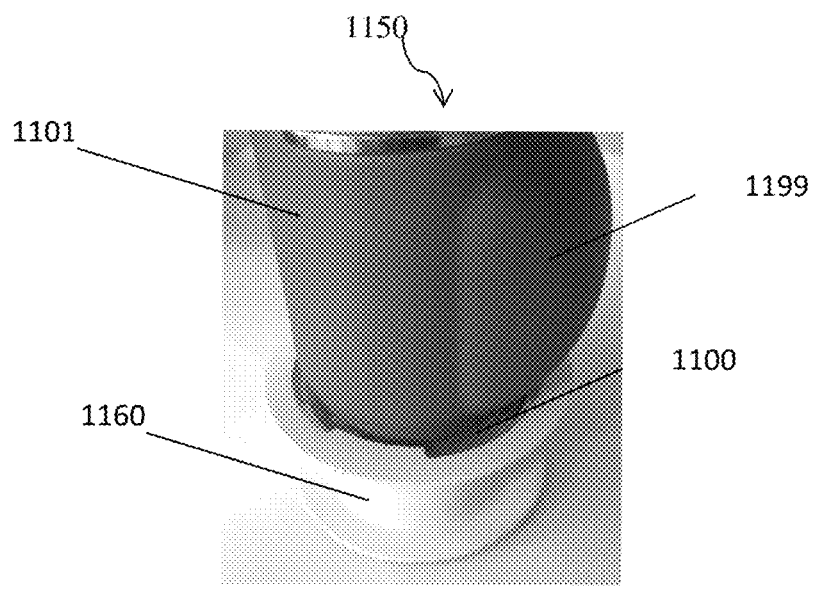
FIG. 11(D) is a photo of an eye imaging apparatus with a hand grip inserted in the plug-in disposable system of FIG. 11(A).

FIG. 11(A) and FIG. 11(B) schematically illustrates a perspective view and a section view of a plug-in disposable system 1150 comprising a disposable cap 1100 and a disposable packaging shell 1160, where the disposable cap 1100 is placed inside the disposable packaging shell 1160. FIG. 11(C) is a photo of an eye imaging apparatus 1101, the disposable cap 1100 and the disposable packaging shell 1160 according to the embodiment of FIG. 11(A). FIG. 11(D) is a photo of the eye imaging apparatus 1101 inserted in the plug-in disposable system 1150 of FIG. 11(A), where the eye imaging apparatus 1101 comprises a hand grip 1199 as described in U.S. patent application Ser. No. 14/312,590, titled "MECHANICAL FEATURES OF AN EYE IMAGING APPARATUS". Unless otherwise noted, reference numerals used in FIG. 11 represent components similar to those illustrated in FIG. 10, with the reference numerals incremental by 100. The disposable cap 1100 can be placed inside the disposable packaging shell 1160 after both of them being manufactured, cleaned and maybe even sterilized, in a clean environment. The packaging shell 1160 can comprise a main portion 1168, a waist 1167, and a head 1169. The inside surface of the packaging shell 1160 can be configured to support the contour of the optical window cover 1122 and the shield 1128 of the disposable cap 1100. The optical window cover 1122 of the disposable cap 1100 can be placed near the head 1169. The indentation 1162 on the head 1169 of the packaging shell 1160 can be configured to support the precise curvature of the concave surface of the optical window cover 1122. The sealing lid 1161 can be used seal the disposable cap 1100 from environment inside the packaging shell 1160. The disposable system 1150 including the packaging shell 1160 and the disposable cap 1100 can go through the sterilization process together, like radiation and ETO.

The disposable cap 1100 can comprise one or more locking projections 1127a. The one or more locking projections 1127a are configured to be clicked into the locking grooves of the imaging apparatus. The disposable cap 1100 can further comprise a spring style of structure 1139 to allow flexibility and extra elongation of the shield 1128 when the locking projections 1127a are locked into the locking grooves. The disposable cap 1100 can further comprise one or more releasing tabs 1127b. The releasing tabs 1127b and the locking projections 1127a can be disposed at the same location on the open end of the disposable cap 1100, where the releasing tabs 1127b extend radially outward away from the optical axis of the imaging apparatus and the locking projections 1127a extend radially inward towards the optical axis. For example, the releasing tabs 1127b and the locking projections 1127a can form a continuous tab in one embodiment. The releasing tab 1127b can have a larger width along the radial direction than the locking projections 1127a in one embodiment.

Referring to FIG. 11(A), the packaging shell 1160 can comprise one or more shell tabs 1165 and open spaces 1164 between the shell tabs 1165. The one or more shell tabs 1165 can be configured to mate with the one or more releasing tabs 1127b of the disposable cap 1100. The one or more shell tabs 1165 can have an L-shape with a curved end extending towards the front direction where the optical window is placed. The shell tabs 1165 can comprise a long portion 1165a that mates with the releasing tabs 1127b of the disposable cap 1160 and is parallel to the releasing tabs 1127b. The shell tabs 1165 can further comprise a short stopper 1165b that is perpendicular to the releasing tabs 1127b. The short stopper 1165b of the shell tab 1165 can be configured as a stopper to stop the rotation of the releasing tabs 1127b. The long portion 1165a can be configured to match the releasing tabs 1127b to detach the disposable cap 1100 from the imaging apparatus.

After a cleaning/disinfection process, the disposable cap 1100 can be placed into the packaging shell 1160. The disposable cap 1100 can be rotational movable with respect to the disposable packaging shell 1160 between an open position and a storage position. The one or more radially outward releasing tabs 1127b are disposed underneath open spaces 1164 in the open position and underneath the one or more radially inward shell tabs 1165 in the storage position. The disposable cap 1100 can be inserted into the packaging shell 1160 with the releasing tabs 1127b positioned in the open space 1164 between the shell tabs 1165. The disposable cap 1100 can be rotated until the releasing tabs 1127b/locking projections 1127a are underneath the mating shell tabs 1165 and stopped by the short stopper 1165b of the shell tabs 1165, as shown in FIG. 11(A). For example, when the short stopper 1165b can be disposed at the right-hand side of the shell tab 1165 as shown in FIG. 11(A), the disposable cap 1100 can be rotated clock-wise relative to packaging shell 1160 until the releasing tabs 1127b/locking projections 1127a hit the short stoppers 1165b. Then each short stopper 1165b can stop the rotation and prevent further relative movement of the disposable cap 1100 to the packaging shell 1160. In another embodiment, the short stopper 1165b can be disposed at the left-hand side of the shell tab 1165, and the disposable cap 1100 can be rotated counter clock-wise until the short stopper 1165b stops the rotation of the disposable cap 1100. The structures of the shell tabs 1165 are configured to secure the position of the disposable cap 1100 within the packaging shell during transportation.

The packaging shell 1160 can protect the disposable cap 1100 from contamination from environment and provide physical protection during transportation for the disposable cap 1100 to prevent it being crashed accidentally. The packaging shell 1160 can further allow the operator to attach and detach the disposable cap 1100 from the imaging apparatus without contacting the disposable cap 1100 directly. Furthermore, the packaging shell 1160 can provide safe storage for the used cap 1100 which could be contaminated during the examination. In some embodiments, the packaging shell 1160 can comprise an indentation at the head 1162 at the head 1169 of the packaging shell 1160 to protect the concave surface of the optical window cover 1122 of the disposable cap 1100.

As discussed above, the disposable packaging shell 1160 can further comprise an identifying element 1163 with unique identification information (ID). The identifying element 1163 on the disposable packaging shell 1160 can be configured to uniquely identify the disposable cap 1100.

FIGS. 12(A), 12(B), 12(C), 12(D) and 12(E) schematically illustrate the operation process of using the plug-in disposable system 1250 for the eye imaging apparatus 1201. Unless otherwise noted, reference numerals used in FIG. 12 represent components similar to those illustrated in FIG. 11, with the reference numerals incremental by 100.

Figure 12A:
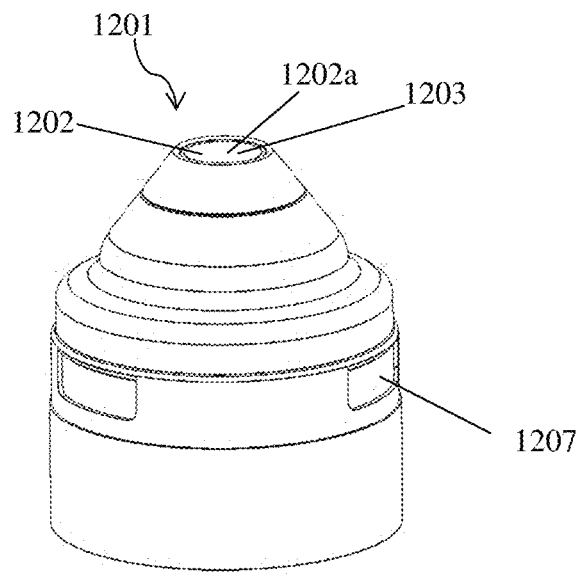
FIG. 12(A) is a perspective view that schematically illustrates a step of an operation process of using the plug-in disposable system for the eye imaging apparatus: placing an index-matching gel on an optical window of the imaging apparatus.

As shown in FIG. 12(A), the image apparatus 1201 can be held with the optical window 1202 pointing up. A drop of special optically clear index-matching gel or liquid 1202a can be dispensed into the center area of the concave surface 1203 of the optical window 1202. The eye imaging apparatus 1201 can comprise a one or more s locking grooves 1207.

Figure 12B:
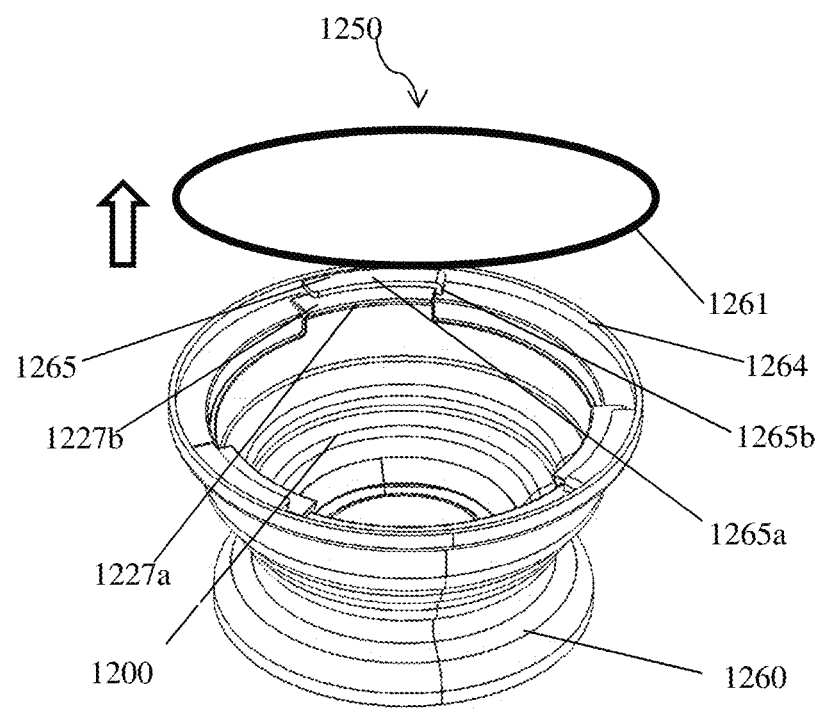
FIG. 12(B) is a perspective view that schematically illustrates a step of an operation process of using the plug-in disposable system for the eye imaging apparatus: opening the sealing lid of the disposable packaging shell.

Referring to FIG. 12(B), the disposable system 1250 can comprise a disposable packaging shell 1260 and a disposable cap 1200. The disposable cap 1200 can comprise one or more locking projections 1227a and one or more releasing tabs 1227b. The disposable packaging shell 1260 can comprise a sealing lid 1261, one or more shell tabs 1265 and open spaces 1264 between the shell tabs 1265. The shell tabs 1265 can comprise a long portion 1265a and a short stopper 1265b as discussed above. The disposable cap 1200 can be inserted into the packaging shell 1260 when the releasing tabs 1227b are positioned in the open space 1264 between the shell tabs 1265. The disposable cap 1200 can be rotated until the releasing tabs 1227*b* are stopped by the short stopper 1265*b* of the shell tabs 1265. The short stopper 1265*b* can stop the movement of the disposable cap 1200 during the transportation because the releasing tabs 1227*b* cannot pass the short stopper 1265*b* in one direction. The disposable cap 1200 can be rotational movable with respect to the disposable packaging shell 1260 between an open position and a storage position. The one or more radially outward releasing tabs 1227*b* are disposed underneath open spaces 1264 in the open position and underneath the one or more radially inward shell tabs 1265 in the storage position.

Before the eye examination or surgery, the sealing lid 1261 for the individual sealed packaging shell 1260 can be opened and peeled off. The shell 1260 not only can protect the single-use disposable cap 1200 from damage during the transportation, but also can help to attach the disposable cap 1200 to and detach the disposable cap 1200 from the imaging apparatus 1201 after the medical procedure. The disposable cap 1200 can comprise one or more locking projections 1227*a* that matches the plurality of locking grooves 1207 of the imaging apparatus 1201. The disposable cap 1200 can further comprise one or more releasing tabs 1227*b* that matches the plurality of L-shape shell tabs 1265 of the packaging shell 1260.

Figure 12C:
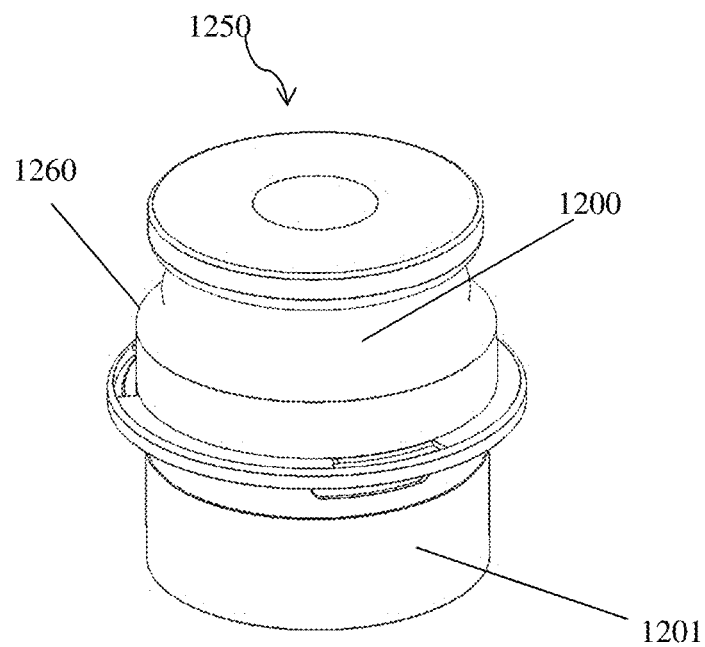
FIG. 12(C) is a perspective view that schematically illustrates a step of an operation process of using the plug-in disposable system for the eye imaging apparatus: placing the disposable packaging shell with the disposable cap over the imaging apparatus.
Figure 12D:
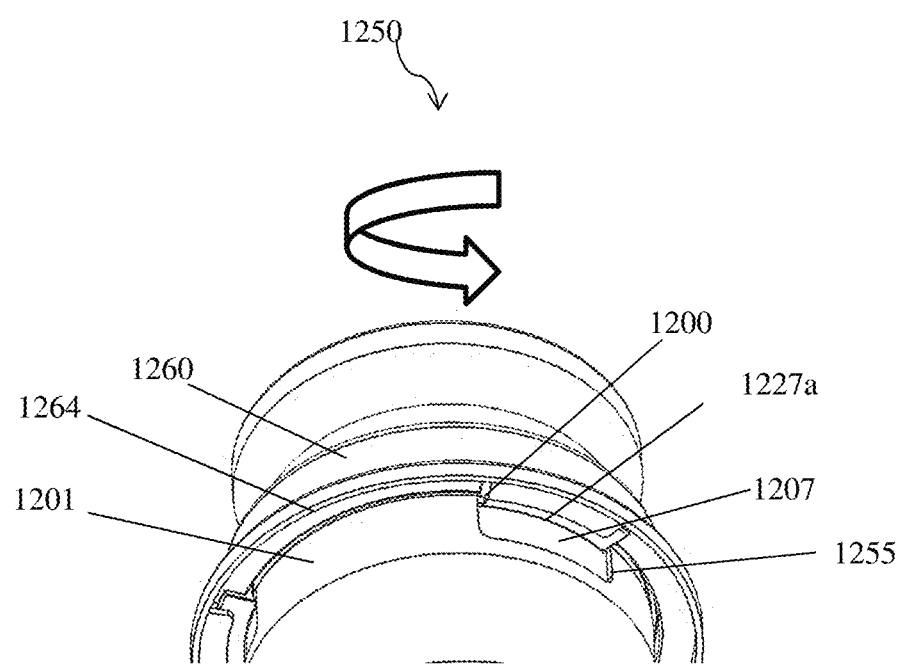
FIG. 12(D) is a perspective view that schematically illustrates a step of an operation process of using the plug-in disposable system for the eye imaging apparatus: moving the disposable packaging shell with the disposable cap relative to the imaging apparatus to lock the disposable cap to the imaging apparatus.

Referring to FIG. 12(C) and FIG. 12(D), the packaging shell 1260 with the disposable cap 1200 inside can be placed over the top of the imaging apparatus 1201. The frontal part of the imaging apparatus 1201 can be simply plugged into the disposable cap 1200 which is secured inside the protective packaging shell 1260. By rotating the shell 1260 relative to the housing of the imaging apparatus 1201 in one direction, the locking projections 1227*a* on the disposable cap 1200 can fall into the matching locking grooves 1207 on the housing of the imaging apparatus 1201. The shell 1260 with the disposable cap 1200 inside can be rotated together relative to the housing of the imaging apparatus 1201 counter clockwise in one embodiment. The shell 1260 with the disposable cap 1200 inside can be rotated relative to the housing of the imaging apparatus 1201 clockwise in another embodiment. The sidewalls 1255 of the locking grooves 1207 can stop the relative rotation and lock the disposable cap 1200 with the housing of the imaging apparatus.

Now referring to FIGS. 12(B), (C) and (D), after the locking projections 1227*a* fall into the locking grooves 1207 of the imaging apparatus 1201, the disposable cap 1200 and the imaging apparatus 1201 can be rotated together in an opposite direction of the short stopper 1265*b* of the shell tabs 1265. For example, as shown in FIG. 12(B), the short stopper 1265*b* can stop the locking projections 1227*a* rotating clockwise. After the locking projections 1227*a* fall into the locking grooves 1207, the disposable cap 1200 and the imaging apparatus 1201 can be rotated together counter clockwise. In another embodiment, the short stopper 1265*b* can stop the locking projections 1227*a* rotating counter clockwise. After the locking projections 1227*a* fall into the locking grooves 1207, the disposable cap 1200 and the imaging apparatus 1201 can be rotated together clockwise. Therefore, the disposable cap 1200 and the imaging apparatus 1201 can be rotated together. The user can turn the imaging apparatus 1201 in the opposite direction of the short stopper 1265*b*. The releasing tabs 1227*b* can be rotated to the open space 1264 between the shell tabs 1265, thus no longer aligned with and blocked by the shell tabs 1265. The imaging apparatus 1201 can then be pulled out from the packaging shell 1260 with the disposable cap 1200 attached to the housing of the imaging apparatus 1201. The user never needs to touch the disposable cap 1200 in the process. The user can release the apparatus 1201 with the disposable cap 1200 from the shell 1260 by simply pulling the imaging apparatus out.

Figure 12E:
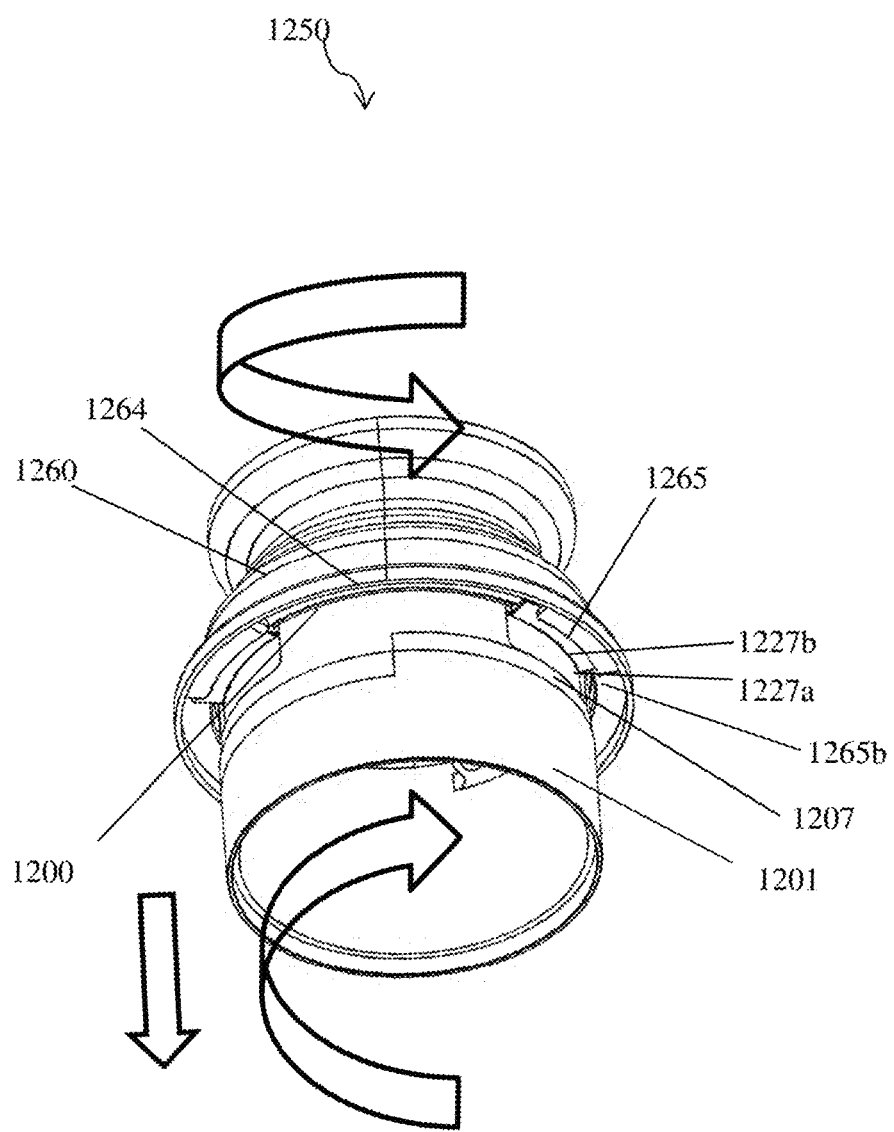
FIG. 12(E) is a perspective view that schematically illustrates a step of an operation process of using the plug-in disposable system for the eye imaging apparatus: moving the imaging apparatus with the disposable cap relative to disposable packaging shell to lock the disposable cap to disposable packaging shell, and pulling the imaging apparatus out of the disposable packaging shell while leaving the disposable cap inside the disposable packaging shell.

Referring to FIG. 12(E), after the examination or surgery is finished, the imaging apparatus 1201 with the disposable cap 1200 can be plugged back into the packaging shell 1260 while the releasing tabs 1227*b*/locking projections 1227*a* of the disposable cap 1200 are aligned with the open space 1264 on the shell 1260. In another embodiment, the packaging shell 1260 can be placed back onto the top of the imaging apparatus 1201 with disposable cap 1200, while the releasing tabs 1227*b* of the disposable cap 1200 are roughly aligned with the opening space 1264 on the packaging shell. Then the packing shell 1260 can be rotated in one direction, for example, the packing shell 1260 can be rotated clockwise as shown in FIG. 12(E), while the body of the imaging apparatus 1201 with the disposable cap 1200 can be held steady. The rotation can be stopped when the releasing tabs 1227*b* from the disposable cap 1200 are stopped by the short stopper 1265*b* of the shell tabs 1265. In another embodiment, the imaging apparatus 1201 with the disposable cap 1200 can be rotated together until the rotation is stopped by the short stopper 1265*b*. Then the releasing tabs 1227*b* of the disposable cap 1200 are aligned with the shell tabs 1265, and the disposable cap 1200 is securely locked back to the shell 1260.

After the releasing tabs 1227*b* of the disposable cap 1200 are aligned with the shell tabs 1265, the user can hold the exterior surface of shell 1260 while pulling the image apparatus 1201 away from the shell 1260. The shell tabs 1265 can block the releasing tabs 1227*b* of the disposable cap 1200, which is equivalent to applying a pulling force to the releasing tabs 1227*b* towards the frontal direction. Accordingly, the locking projections 1227*a* can be pulled out of the locking grooves 1207 of the imaging apparatus 1201, and the disposable cap can be detached from the imaging apparatus 1201. Therefore the imaging apparatus 1201 can be pulled out from the shell 1260, while the disposable cap 1200 can be left behind in the shell 1260. The user can hold the exterior surface of the packaging shell 1260 during the entire process without touching the potentially contaminated disposable cap 1200, especially the exterior surface of the disposable cap 1200. The disposable cap 1200 can be kept in the packaging shell 1260 and disposed together.

The packaging shell 1260 can provide more thorough protection of the disposable cap 1200 from possible contamination during the medical procedure because the user never needs to touch the disposable cap 1200 during the installation process. In addition, attaching the disposable cap 1200 to the imaging apparatus 1201 using the plug-in method by the shell 1200 can have a quick turn-around time. The packaging shell 1260 can also protect the disposable cap 1200 during the sterilization process and the transportation process, and protect users from contamination after the medical procedure.

The plug-in disposable system can have various embodiments with different locking and unlocking elements, or different attaching and releasing structures, not limited to the structures discussed above. For example, in an alternative embodiment, only one single continuous locking groove 1207 is constructed on the apparatus housing while plurality of locking projections 1227*a* are used. The friction between the locking projections 1227*a* and surface of the locking groove 1207 can be sufficient to prevent the rotation of the disposable cap 1200 relative to the apparatus housing during the attaching and detaching operation. In another example, after an imaging apparatus is plugged into a disposable system comprising a disposable cap and a disposable packaging shell, the disposable cap can be locked with the imaging apparatus by a locking groove on the disposable cap and a plurality of locking projections on the housing of the imaging apparatus in other embodiments. In another embodiment, the packaging shell can comprise a locking groove to be locked with the disposable cap, and the packaging shell can further comprise extended taps to help unlock the shell from the disposable cap.

Figure 13:
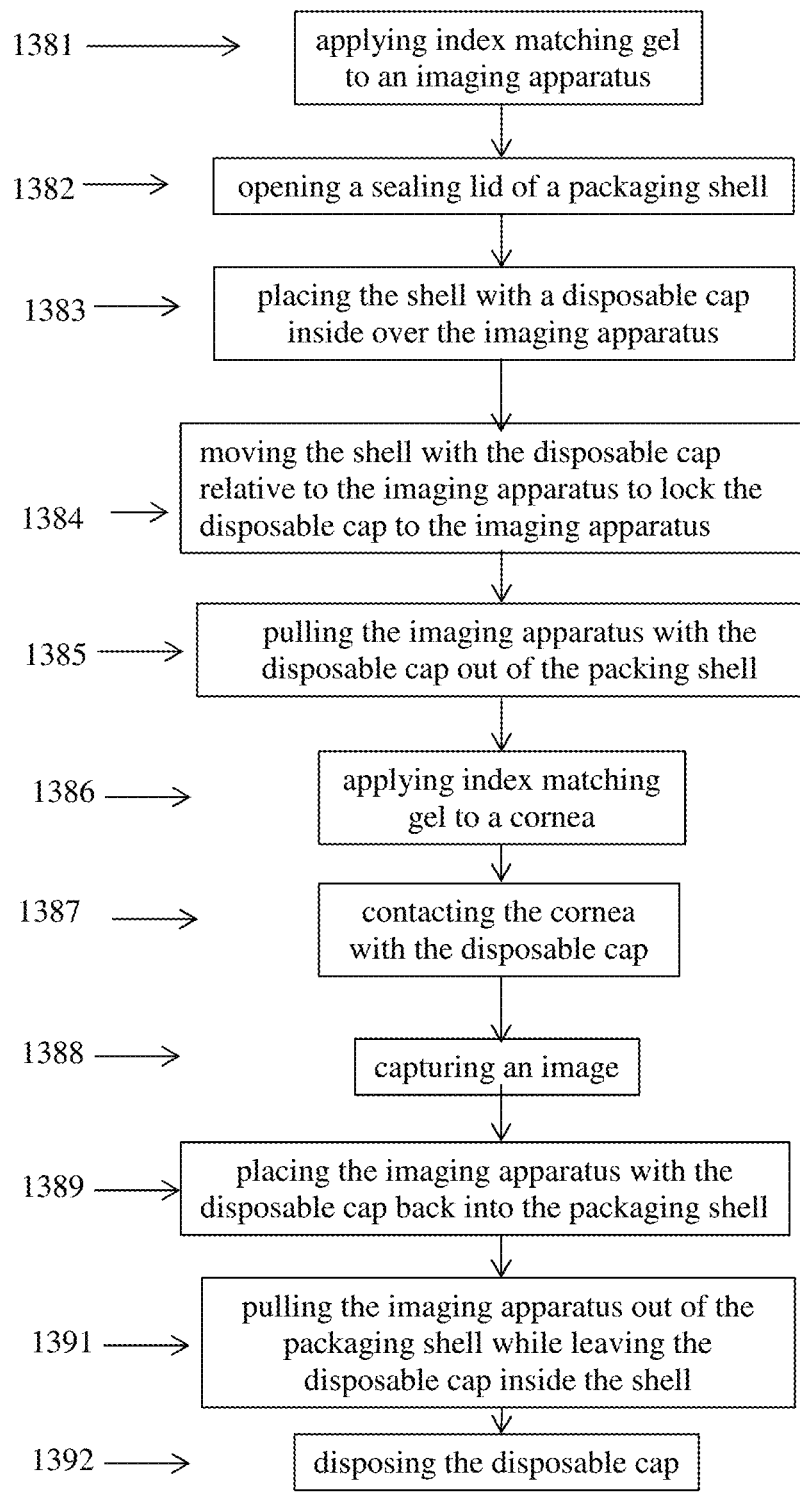
FIG. 13 is a flow chart of a method of using a plug-in disposable system to prevent cross-contamination from using an eye imaging apparatus.

FIG. 13 is a block diagram which schematically illustrates an exemplary method 1380 of using a plug-in disposable system to prevent cross-contamination from using an eye imaging apparatus. The method comprises the following steps. First, applying an index matching gel or liquid to a front surface of the optical window of the eye imaging apparatus as shown in block 1381, where the eye imaging apparatus comprises a plurality of locking grooves and is pointing up with the optical window at its top.

The method comprises opening a sealing lid of a disposable packaging shell of a disposable system, as shown in block 1382. The disposable system can further comprise a disposable cap. The disposable cap can comprise a locking element that matches a locking element of the imaging apparatus. The disposable cap can comprise a releasing structure that matches a releasing structure of the packaging shell. For example, the disposable cap can comprise a plurality of locking projections that match a plurality of grooves on the packaging shell, and a plurality of releasing tabs that matches the shell tabs in one embodiment.

The method comprises placing the disposable system including the packaging shell and the disposable cap over the optical window of the eye imaging apparatus, as shown in block 1383. The frontal part of the imaging apparatus can be plugged into the disposable cap inside the packaging shell.

The method further comprises moving the packaging shell with the disposable cap relative to the imaging apparatus until the locking elements of the disposable cap and the imaging apparatus click to activate the locking element of the disposable cap, thus the disposable cap is locked to the imaging apparatus. For example, the method can comprise rotating the shell relative to the imaging apparatus or rotating the imaging apparatus until the locking projections on the disposable cap fall into the matching locking grooves of the imaging apparatus in one embodiment. See block 1384.

The method comprises pulling the imaging apparatus with the disposable cap out of the packing shell, as shown in block 1385. The method can further comprise rotating the imaging apparatus and the disposable cap together to unlock the disposable cap from the packaging shell prior to removing the disposable cap from the shell. In one embodiment, the disposable cap and the imaging apparatus can be rotated together until releasing tabs of the cap reach the open spaces between the shell tabs. The user can then release the apparatus with the disposable cap thereon from the shell by simply pulling the imaging apparatus out with the disposable cap.

The example method then comprises applying an index-matching gel to a cornea of an eye of a patient, as well as concave surface of the disposable cap, then contacting the cornea with the disposable cap on the eye imaging apparatus and capturing an image of the eye, as in blocks 1386-1388.

The method can comprise placing the imaging apparatus with the disposable cap back into the packaging shell after the medical procedure as in block 1389. In one embodiment, the imaging apparatus with the disposable cap is placed back into the packaging shell while the releasing tabs of the disposable cap are aligned with the open spaces on the shell.

The method can further comprise pulling the imaging apparatus out of the packaging shell while leaving the disposable cap inside the shell, as in block 1391. In one embodiment, the imaging apparatus with the disposable cap can be rotated together until the rotation is stopped by the short stoppers of the shell tabs and the releasing tabs of the disposable cap are aligned with the shell tabs. Then the imaging apparatus can be pulled out from the shell, while the disposable cap can be left behind in the shell.

The method can further comprise disposing the packaging shell with the disposable cap inside, see block 1392. Each disposable system including the disposable cap and the packaging shell can be single use to prevent cross-contamination among the patients.

Various embodiments further disclose a method of using unique identification (ID) for each single-use disposable cap. As discussed above, the disposable packaging shell can further comprise an identifying element with unique ID. The identifying element on the disposable packaging shell can be configured to uniquely identify the individual disposable cap. A barcode, two dimensional identification pattern, or radio frequency identification chip can be printed to, or embodied into the body of the packaging shell, to uniquely identify each individual disposable cap. Each ID can be associated with each individual disposable cap and can be shown on the sterile packaging shell or printed on the sealing lid. Alternatively or in conjunction with the ID on the packaging shell, an ID can be placed directly on or in the disposable cap itself. The ID can be used to prevent counterfeit or fake product in the medical practices, and/or may be used to prevent a disposable cap from being used more times than it is designed to be used.

Figure 14:
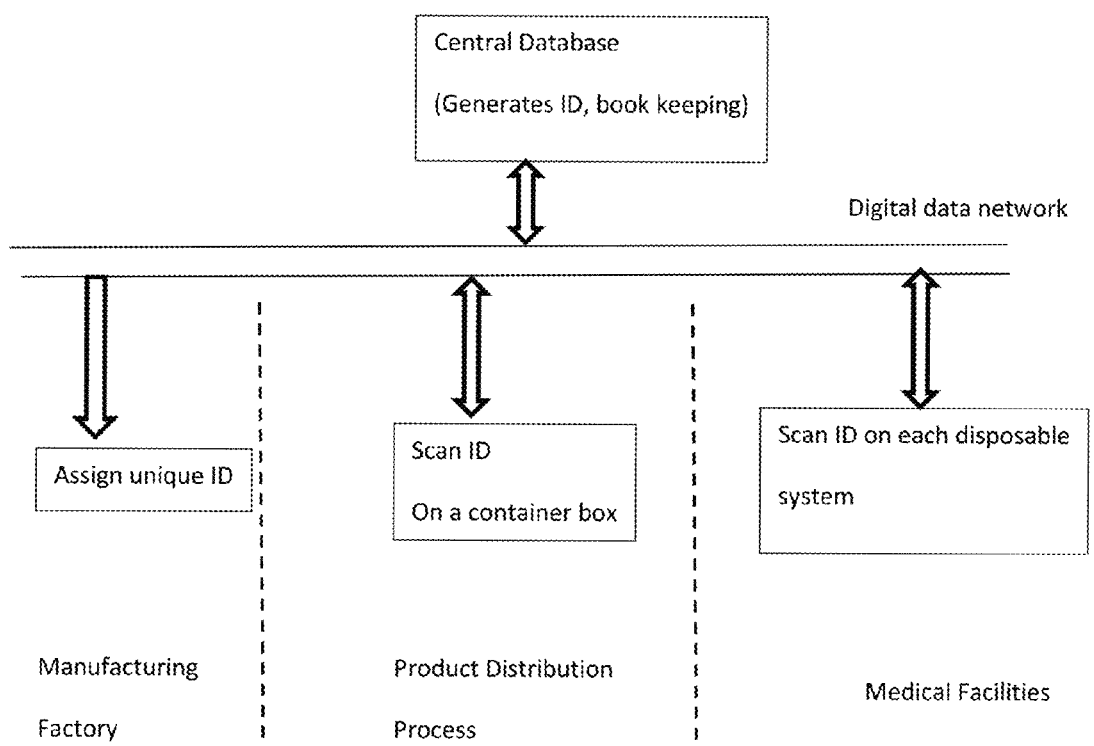
FIG. 14 is block diagram that schematically illustrates the use of an ID on each disposable cap according to one embodiment of the disclosure.

FIG. 14 schematically illustrates a flow diagram of a method of tracking of individual disposable system. In some embodiments, as shown in FIG. 14, a unique ID of each disposable system can be generated by a central database and then assigned to each individual disposable system during the manufacturing process. Another unique ID can be assigned to each eye imaging apparatus as well. Yet another unique ID can be assigned to a container box which houses multiple units of disposable systems, for example, every 12 units or 100 units etc. After the box is shipped out from a factory or distributor, the tracking of individual disposable systems can be accomplished by recording the ID on the container box. When a hospital orders a box of disposable systems, the ID of the box can be input into the central data base and matched with the ID of one or more imaging apparatuses registered to the hospital. A special code may be either provided with the shipped container or sent directly to the imaging apparatus(es) at the destination hospital electronically. The special code can be configured to be related to the ID(s) of individual disposable systems and/or the ID(s) of the imaging apparatus(es). In some embodiments, the special code can be configured to be unique to the combination of the IDs of the individual disposable systems and the ID(s) of the specific imaging apparatus(es). In some embodiments, the special code can be the encrypted ID(s) of the disposable systems. When the container box is received by the hospital, the camera, or radio frequency sensor and associated software of the imaging apparatus may be used to identify the ID of each box or each disposable system. After inputting the special code either accompanying the box or sent directly from the central database electronically, the ID can be compared with the authentic list of IDs provided by the manufactures. The authentic list of IDs can reside in a local imaging apparatus, or maintained on the central database and can be reached through the internet.

The identification information (ID) can be used as a "lock key" to allow a user to operate the eye imaging apparatus. If a positive identification is detected, the imaging apparatus can be allowed to perform the medical procedures, such as imaging the eyes of the patients for eye examination or surgeries. Otherwise, the eye imaging apparatus cannot be operated. Furthermore, an alert can be sent to the user and/or a central tracking system.

The ID information can also be used to ensure the disposable system is single use to prevent cross-contamination among the patients. Each disposable system including the disposable cap and the disposable packaging shell may be provided with unique ID information. The identifying element on the disposable packaging shell can be configured to uniquely identify the disposable cap. Each unique ID can be invalidated from the authentic list after the ID has been used once (or another predetermined number of times.)

In some embodiments, the ID on the container box which houses multiple units of disposable systems, the ID on the imaging apparatus, and/or the special code described above may be omitted. In such embodiments, the imaging apparatus may simply read the ID on the disposable cap and/or shell and compare it with an authentic list stored in the imaging apparatus or obtained from a computer network.

While the present disclosure has been disclosed in example embodiments, those of ordinary skill in the art will recognize and appreciate that many additions, deletions and modifications to the disclosed embodiments and their variations may be implemented without departing from the scope of the disclosure.

A wide range of variations to those implementations and embodiments described herein are possible. Components and/or features may be added, removed, rearranged, or combinations thereof. Similarly, method steps may be added, removed, and/or reordered.

Likewise various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Accordingly, reference herein to a singular item includes the possibility that there are a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below.

Additionally as used herein, a phrase referring to "at least one of" a list of items refers to any combination of those items, including single members. As an example, "at least one of: a, b, or c" is intended to cover: a, b, c, a-b, a-c, b-c, and a-b-c.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be described as occurring in a particular order, this should not be understood as requiring that such operations be performed in the particular order described or in sequential order, or that all described operations be performed, to achieve desirable results. Further, other operations that are not disclosed can be incorporated in the processes that are described herein. For example, one or more additional operations can be performed before, after, simultaneously, or between any of the disclosed operations. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single product or packaged into multiple products. Additionally, other embodiments are within the scope of the following claims. In some cases, the actions recited in the claims can be performed in a different order and still achieve desirable results.

What is claimed is:

1. A disposable cap for an eye imaging apparatus with an optical window, the disposable cap configured to be in contact with an eye of a patient, the disposable cap having an open end at a proximal end and a covering end at a distal end, the disposable cap comprising:
  an optically transparent window cover comprising a concave front surface and a convex back surface, the convex back surface configured to match a concave shape of a front surface of the optical window of the eye imaging apparatus;
  a flat ring extending radially outward from the optically transparent window cover to a distal ridge, the flat ring having a distally facing ring surface and a proximally facing surface configured to fit a flat ring of the optical window;
  a distal ridge extending further distally and radially outwardly from the flat ring, the distal ridge having a proximal surface disposed distal to the distally facing ring surface and adapted to engage with a corresponding ridge of the eye imaging apparatus, the distal ridge configured to be a buffer to absorb a pulling force to prevent the optical window cover from bulging and keep the convex back surface in shape;
  a side wall extending proximally and radially outwardly from the distal ridge toward the open end, the side wall adapted to engage with a housing of the eye imaging apparatus; and
  a locking element comprising
    a plurality of radially inward projections disposed at the open end, the plurality of projections movably supported with respect to the side wall and configured to latch onto a plurality of locking grooves of the eye imaging apparatus to attach the disposable cap to the eye imaging apparatus; and
    a plurality of radially outward releasing tabs disposed at a same position and an opposite side of the plurality of projections at the open end, wherein the plurality of releasing tabs configured to detach the disposable cap from the eye imaging apparatus, wherein a width of the plurality of releasing tabs is larger than a width of the plurality of projections; and wherein a length of the disposable cap from the distal end to the plurality of projections is shorter than a length of a portion of the eye imaging apparatus from a distal end of the eye imaging apparatus to the plurality of locking grooves.

2. The disposable cap in claim 1, wherein the flat ring is configured to be an alignment reference to match the flat ring of the optical window and form a supporting pad for the distal ridge.

3. The disposable cap in claim 1, wherein the optically transparent window cover, the flat ring, the distal ridge and the side wall are a single integral material.

4. The disposable cap in claim 1, wherein the plurality of radially inward projections have a length between 3 mm and 28 mm, a width between 0.5 mm and 3 mm, a thickness between 1 mm and 10 mm.

5. The disposable cap in claim 1, further comprising a shield extending proximally from the side wall to the locking element.

6. The disposable cap in claim 5, wherein the shield comprises at least one of thermoplastic elastomer (TPE), rubber, plastic, latex, vinyl, nitrile and polymer.

7. The disposable cap in claim 5, wherein the optically transparent window cover, the flat ring, the distal ridge, the side wall and the shield are a single integral material.

8. The disposable cap in claim 5, wherein the shield further comprises a spring style bellow ring, the spring style bellow ring comprising at least one corner of 90 degrees.

9. The disposable cap in claim 5, wherein the radially inward projection is movably supported with respect to a side wall of the shield.

10. The disposable cap in claim 5, further comprising a sheath proximally and radially outwardly from the shield, the disposable cap adapted to cover the entire eye imaging apparatus.

11. The disposable cap in claim 10, wherein the sheath comprises a at least one of thermoplastic elastomer (TPE) and rubber.

12. The disposable cap in claim 10, wherein the optically transparent window cover, the flat ring, the distal ridge, the side wall, the shield and the sheath are a single integral material.

13. The disposable cap in claim 1, wherein the plurality of radially outward releasing tabs have a length between 6 mm and 60 mm, a width between 1 mm and 10 mm, and a thickness between 0.5 mm and 4 mm.

14. The disposable cap in claim 1, wherein a thickness of the window cover is between from about 0.01 mm to 3 mm.

15. The disposable cap in claim 1, wherein the window cover comprises a thermal plastic material including Polycarbonate (PC).

16. A plug-in disposable system for an eye imaging apparatus with an optical window and a plurality of locking grooves, the plug-in disposable system comprising:
a disposable cap configured to be in contact with an eye of a patient, the disposable cap having an open end at a proximal end and a covering end at a distal end, the disposable cap comprising:
an optically transparent window cover comprising a concave front surface and a convex back surface;
a flat ring extending radially outward from the optically transparent window cover to a distal ridge, the flat ring having a distally facing ring surface and a proximally facing surface configured to fit a flat ring of the optical window;
a distal ridge extending further distally and radially outward from the flat ring, the distal ridge having a proximal surface disposed distal to the distally facing ring surface and adapted to engage with a corresponding ridge of the eye imaging apparatus, the distal ridge configured to be a buffer to absorb a pulling force to prevent the optical window cover from bulging and keep the convex back surface in shape;
a side wall extending proximally and radially outwardly from the distal ridge toward the open end;
a locking element comprising
a plurality of radially inward projections disposed at the open end, the plurality of projections movably supported with respect to the side wall and configured to latch onto the plurality of locking grooves of the eye imaging apparatus by a latching action and attach the disposable cap to the eye imaging apparatus; and
a plurality of radially outward releasing tabs disposed at a same position and an opposite side of the plurality of projections at the open end and configured to detach the disposable cap from the eye imaging apparatus; wherein a width of the plurality of releasing tabs is larger than a width of the plurality of projections; and
a disposable packaging shell of the disposable cap, the disposable packaging shell comprising:
a sealing lid at a top end;
a head extending outward at a bottom end; and
a plurality of radially inward shell tabs disposed at the top end and a plurality of open spaces therebetween, the plurality of radially inward shell tabs adapted to mate with the plurality of radially outward releasing tabs;
wherein the disposable cap is rotationally movable with respect to the disposable packaging shell;
wherein the plurality of radially outward releasing tabs configured to be rotatable to be aligned with the plurality of open spaces to enable the disposable cap being pulled out of the packaging shell along with the eye imaging apparatus by the latching action, and further rotatable to be underneath the plurality of radially inward shell tabs to enable the plurality of radially inward shell tabs applying a pulling force to the plurality of releasing tabs to unlatch the plurality of locking projections out of the plurality of locking grooves, thereby detaching the disposable cap from the eye imaging apparatus.

17. The plug-in disposable system in claim 16, wherein the plurality of radially inward shell tabs have an L-shape, the plurality of radially inward shell tabs comprising a long portion extending along a tangential direction of the open end, the short stopper being a curved end extending towards a front direction and parallel to the optical axis configured to stop the rotation of the plurality of releasing tabs.

18. The plug-in disposable system in claim 16, wherein the head comprises an indentation at a center portion, the indentation comprising a convex inside surface adapted to match the concave front surface of the window cover of the disposable cap.

19. The plug-in disposable system in claim 16, wherein the window cover further comprises a flat, distally facing ring surface extending radially outward from the convex back surface to the distal ridge.

20. The plug-in disposable system in claim 16, wherein the disposable cap further comprises a shield extending proximally from the side wall to the locking element.

21. The plug-in disposable system in claim 20, wherein the shield further comprises a spring style bellow ring, the spring style bellow ring comprising at least one corner.

22. The plug-in disposable system in claim 16, wherein the disposable cap further comprises a sheath proximally and radially outwardly from the shield, the disposable cap adapted to cover the entire eye imaging apparatus.

23. The plug-in disposable system in claim 16, wherein the disposable packaging shell further comprises an identifying element containing unique identification information.

* * * * *